(12) United States Patent
Van Zandt et al.

(10) Patent No.: US 10,906,872 B2
(45) Date of Patent: Feb. 2, 2021

(54) METHOD OF PREPARING (3R,4S)-3-ACETAMIDO-4-ALLYL-N-(TERT-BUTYL)PYRROLIDINE-3-CARBOXAMIDE

(71) Applicant: CALITHERA BIOSCIENCES, INC., South San Francisco, CA (US)

(72) Inventors: Michael C. Van Zandt, Guilford, CT (US); Jennifer L. Savoy, Killingworth, CT (US)

(73) Assignee: Calithera Biosciences, Inc., South San Francisco, CA (US)

(*) Notice: Subject to any disclaimer, the term of this patent is extended or adjusted under 35 U.S.C. 154(b) by 0 days.

(21) Appl. No.: 16/687,394

(22) Filed: Nov. 18, 2019

(65) Prior Publication Data

US 2020/0087255 A1  Mar. 19, 2020

Related U.S. Application Data

(62) Division of application No. 15/977,948, filed on May 11, 2018, now Pat. No. 10,494,339.

(60) Provisional application No. 62/505,282, filed on May 12, 2017.

(51) Int. Cl.

| C07D 207/16 | (2006.01) |
|---|---|
| C07D 207/06 | (2006.01) |
| C07C 233/05 | (2006.01) |
| C07C 233/57 | (2006.01) |
| C07B 57/00 | (2006.01) |
| C07C 233/65 | (2006.01) |
| C07C 235/06 | (2006.01) |
| C07F 5/02 | (2006.01) |
| C07C 231/12 | (2006.01) |
| C07C 327/22 | (2006.01) |

(52) U.S. Cl.
CPC ............ *C07D 207/16* (2013.01); *C07B 57/00* (2013.01); *C07C 231/12* (2013.01); *C07C 233/05* (2013.01); *C07C 233/57* (2013.01); *C07C 233/65* (2013.01); *C07C 235/06* (2013.01); *C07C 327/22* (2013.01); *C07D 207/06* (2013.01); *C07F 5/025* (2013.01); *C07B 2200/07* (2013.01); *C07B 2200/13* (2013.01)

(58) Field of Classification Search
CPC .................................................. C07D 207/16
See application file for complete search history.

(56) References Cited

U.S. PATENT DOCUMENTS

| 8,894,970 | B2 | 11/2014 | Tomczuk et al. |
|---|---|---|---|
| 9,200,011 | B2 | 12/2015 | Van Zandt et al. |
| 9,233,985 | B2 | 1/2016 | Van Zandt et al. |
| 9,266,908 | B2 | 2/2016 | Van Zandt et al. |
| 9,440,995 | B2 | 9/2016 | Van Zandt et al. |
| 10,494,339 | B2 * | 12/2019 | Van Zandt ............ C07C 235/06 |
| 2002/0081626 | A1 | 6/2002 | Kaddurah-Daouk et al. |
| 2004/0063666 | A1 | 1/2004 | Christianson et al. |
| 2010/0189644 | A1 | 7/2010 | Christianson et al. |
| 2012/0083469 | A1 | 4/2012 | Van Zandt et al. |
| 2012/0129806 | A1 | 5/2012 | Van Zandt et al. |
| 2014/0371175 | A1 | 12/2014 | Van Zandt et al. |
| 2015/0080341 | A1 | 3/2015 | Van Zandt et al. |
| 2015/0191492 | A1 | 7/2015 | Van Zandt et al. |
| 2016/0375044 | A1 | 12/2016 | Gross et al. |

FOREIGN PATENT DOCUMENTS

| CA | 2431080 A1 | 12/2004 |
|---|---|---|
| CN | 103068830 A | 4/2013 |
| CN | 103402549 A | 11/2013 |
| CN | 105879030 A | 8/2016 |
| WO | WO 1999019295 A1 | 4/1999 |
| WO | WO 2007005620 A2 | 1/2007 |
| WO | WO 2010085797 A2 | 7/2010 |
| WO | WO 2011133653 A1 | 10/2011 |
| WO | WO 2012058065 A1 | 5/2012 |
| WO | WO 2012091757 A1 | 7/2012 |
| WO | WO 2013059437 A1 | 4/2013 |
| WO | WO 2013059587 A1 | 4/2013 |
| WO | WO 2013158262 A1 | 10/2013 |
| WO | WO 2015061752 A1 | 4/2015 |
| WO | WO 2016153078 A1 | 9/2016 |
| WO | WO 2016210106 A1 | 12/2016 |

OTHER PUBLICATIONS

Ajinomoto Amino Acids Link News Aug. 2005 vol. 11: 3-4.
Arina, A. et al. 2014 "Adoptively Transferred Immune T Cells Eradicate Established Tumors despite Cancer-Induced Immune Suppression," *J Immunol* 192: 1286-1293.
Baggio et al. 1997 "Inhibition of Mn2+ 2-Arginase by Borate Leads to the Design of a Transition State Analogue Inhibitor, 2(S)-Amino-6-boronohexanoic Acid," *J Am Chem Soc* 119(34): 8107-8108.
Barbul, A. 1990 "Arginine and Immune Function," Nutrition 6(1) 53-58.
Bartolucci et al. 2012 "Direct, Regioselective and Chemoselective Preparation of Novel Boronated Tryptophans by Friedel-Crafts Alkylation" *Organic Letters* 14(2): 600-603.
Busnel et al. 2005 "Synthesis and evaluation of new co-borono-a-amino acids as rat liver arginase inhibitors," *Bioorg Med Chem* 13(7): 2373-2379.
Calithera Biosciences, Inc. Poster, SITC Conference; Nov. 9-13, 2016; National Harbor, MD.
Calithera Biosciences, Inc. Poster, EORTC-NCI-AACR; Nov. 29-Dec. 2, 2016; Munich, Germany.

(Continued)

*Primary Examiner* — Golam M Shameem
(74) *Attorney, Agent, or Firm* — Carl A. Morales; Seth E. Snyder; Dechert LLP

(57) ABSTRACT

A method is provided to conveniently separate racemic (3R,4S)-3-acetamido-4-allyl-N-(tert-butyl)pyrrolidine-3-carboxamide and (3S,4R)-3-acetamido-4-allyl-N-(tert-butyl)pyrrolidine-3-carboxamide using selective crystallization with chiral carboxylic acids.

27 Claims, 9 Drawing Sheets

(56) References Cited

OTHER PUBLICATIONS

CAS Registry Number: 1374395-07-9. CA Index Name: "3-Pyrrolidinecarboxylic acid, 3-amino-4-(3-boronopropyl)-14(5,7-dichloro-1,2,3,4-tetrahydro-3-isoquinolinyl)carbonyll-, (3R,4S)-rel-". STN Entry Date: May 24, 2012 (Last update: May 28, 2012).
Colleluori et al. 2001 "Classical and Slow-Binding Inhibitors of Human Type II Argmase", *Biochem*, 40(31): 9356-9362.
Curtis, B. et al. 2013 "Secondary amines containing one aromatic nitro group: preparation, nitrosation, sustained nitric oxide release, and the synergistic effects of released nitric oxide and an arginase inhibitor on vascular smooth muscle cell proliferation," *Bioorganic & medicinal chemistry* 21(5) 1123-1135. Retrieved from: <https://www.ncbi.nlm.nih.gov/pmc/articles/PMC3574223/pdf/nihms434525.pdf>.
Ellyard et al. 2010 "Alternatively Activated Macrophage Possess Antitumor Cytotoxicity That Is Induced by IL-4 and Mediated by Arginase-1," *J Immunother* 33:443-452.
Geiger, Roger et al. 2016 "L-Arginine Modulates T Cell Metabolism and Enhances Survival and Anti-tumor Activity," *Cell, Cell Press* 167(3): 829ff.
Gritli-Linde, A. et al. 1998 "Opposing effects of suramin and DL-alpha-difluoromethylornithine on polyamine metabolism contribute to a synergistic action on B16 melanoma cell growth in vitro," *Anticancer Research* 18(2A) 863-870.
Hörig et al. 2004 "From bench to clinic and back: Perspective on the 1st IQPC Translational Research conference," *J Translational Med*, 2:44 doi:10.1186/1479-5876-2-44.
Ilies et al. 2011 "Binding of alpha,alpha-Disubstituted Amino Acids to Arginase Suggests New Avenues for Inhibitor Design," *J Med Chem* 54(15): 5432-5443.
Ivanenkov et al. 2014 "Small-molecule arginase inhibitors," *Pharm Pat Anal* 3(1): 65-85.
Kabalka et al. 2008 "Synthesis of a series of boronated unnatural cyclic amino acids as potential boron neutron capture therapy agents," *Appl Organomet Chem*, 22(9): 516-522.
Koziara et al. 2004 "Paclitaxel nanooparticles for the potential treatment of brain tumors," *J Controlled Release* 99: 259-269.
Lei et al. 2009 "Progress of Boronic Acids as Enzyme Inhibitors" *Chinese J Pharm* 40(3): 213-219 (English Abstract only).
Li, L. et al. "An Engineered Arginase FC Protein Inhibits Tumor Growth In Vitro and In Vivo," *Evidence-Based Complementary and Alternative Medicine* vol. 2013, Article ID 243129: 1-9.
Lorvik, Kristina Berg et al. 2016 "Adoptive Transfer of Tumor-Specific Th2Cells Eradicates Tumors by Triggering an in Situ Inflammatory Immune Response," *Cancer Research* 76(23): 6864-6876.
Raber, P. et al. 2012 Metabolism of L-Arginine by Myeloid-Derived Suppressor Cells in Cancer: Mechanisms of T cell suppression and Therapeutic Perspectives *Immunol Invest* 41(6-7): 614-634.
Raber, P. et al. 2016 "T cells conditioned with MDSC show an increased anti-tumor activity after adoptive T cell base immunotherapy," *Oncotarget* 7(14): 17565-17578.
Rodriguez, P. et al. 2003 "L-Arginine Consumption by Macrophages Modulates the Expression of $CD3\chi$ Chain in T Lymphocytes," *J Immunol* 171: 1232-1239.
Rodriguez, P. et al. 2004 "Arginase I Production in the Tumor Microenvironment by Mature Myeloid Cells Inhibits T-Cell Receptor Expression and Antigen-Specific T-Cell Responses," *Cancer Research* 64: 5839-5849.
Rodriguez, P. et al. 2008 "Arginine regulation by myeloid derived suppressor cells and tolerance in cancer: mechanisms and therapeutic perspectives," *Immunol Rev* 222: 180-191.
Rossnagl, Stephanie et al. 2016, "EDA-Fibronectin Originating from Osteoblasts Inhibits the Immune Response against Cancer," *PLOS Biology* 14(9): e1002562.
Sandgren, S. and Belting, M. 2003 "Suramin Selectively inhibits carcinoma cell growth that is dependent on extracellular polyamines," *Anticancer Research* 23(2B): 1223-1228.
Schafer, et al. 2008 "Failure is an option: learning from unsuccessful proof-of-concept trials," *Drug Discov Today*, 13(21): 913-916.
Scheit, K. and Bauer, G. 2014 "Synergistic effects between catalase inhibitors and modulators of nitric oxide metabolism on tumor cell apoptosis," *Anticancer Research* 34(10): 5337-5350. Retrieved from: <https://ar.iiarj ournals.org/content/34/10/5337.full.pdf+html>.
Segal et al. 2012 "Chronic Oral Administration of the Arginase Inhibitors 2(S)-amino-6-boronohexanoic Acid (ABH) Improves Erectile Function in Aged Rates," *J Androl*, 33(6): 11691175.
Selamnia, M. et al. 1998 "α-Difluoromethylornithine (DFMO) as a potent arginase activity inhibitor in human colon carcinoma cells," *Biochemical pharmacology* 55(8): 1241-1245.
Singh, S. et al. 2000 "Arginase Activity in Human Breast Cancer Cell Lines: $N^{\omega}$-*Hydroxy-L-arginine Selectively Inhibits Cell Proliferation and Induces Apoptosis in MDA-MB-468 Cells*" *Cancer Research* 60: 3305-3312.
Steggerda, Susanne M. et al. 2016 "Abstract B045: Arginase inhibitor CB-1158 elicits immune-mediated antitumor responses as a single agent and in combination with other immunotherapies," Second CRI-CIMT-EATI-AACR International Cancer Immunotherapy Conference: Translating Science into Survival; Sep. 25-28, 2016; New York, NY.
Steggerda, Susanne M. et al. 2017, "Inhibition of arginase by CB-1158 blocks myeloid cell-mediated immune suppression in the tumor microenvironment," *Journal for ImmunoTherapy of Cancer* 5(1): 1-18.
Steppan et al. 2013 "Development of novel arginase inhibitors for therapy of endothelial dysfunction," *Front Immunol* 51(4): 5905-5908.
Tate et al. 2008 "Effect of arginase II on L-arginine depletion and cell growth in murine cell lines of renal cell carcinoma," *J Hematol Oncol* 1(14): 1-10.
Vissers, Y. et al. 2005 "Plasma arginine concentrations are reduced in cancer patients: evidence for arginine deficiency?" *Am J Clin Nutr* 81: 1142-1146.

\* cited by examiner

METHOD OF PREPARING (3R,4S)-3-ACETAMIDO-4-ALLYL-N-(TERT-BUTYL)PYRROLIDINE-3-CARBOXAMIDE

CROSS REFERENCE TO RELATED APPLICATIONS

This application is a divisional of U.S. application Ser. No. 15/977,948, filed May 11, 2018, now U.S. Pat. No. 10,494,339, which claims benefit under 35 U.S.C. § 119(e) of U.S. Provisional Application No. 60/505,282, filed May 12, 2017, the contents of all of which are incorporated herein in their entireties by reference thereto.

BACKGROUND

Highly functionalized pyrrolidine based arginase inhibitors have been described in U.S. Patent Publication No. 2017/0121352. For instance, U.S. Patent Publication No. 2017/0121352 describes the synthesis of potent arginase inhibitors such as (3R,4S)-1-(L-alanyl)-3-amino-4-(3-boronopropyl)pyrrolidine-3-carboxylic acid. These ring-constrained arginase inhibitors have tremendous potential as novel therapeutics for a wide variety of diverse diseases such as cancer, asthma, cystic fibrosis, myocardial reperfusion injury, sickle cell anemia, erectile dysfunction, and leishmaniasis. A description of the role of arginase in these diseases can be found in numerous papers, review articles and patents, including U.S. Pat. No. 9,200,011 (Ring constrained analogs as arginase inhibitors), Trends Pharmacol. Sci. 2015, 36(6): 395-405 ("Arginase: an old enzyme with new tricks"), and Clinical and Experimental Immunology 2012, 167: 195-205 ("Immunology in the clinic review series; focus on cancer: tumor-associated macrophages: undisputed stars of the inflammatory tumor microenvironment").

Although these ring-constrained arginase inhibitors have tremendous potential as new treatments for various diseases, they contain multiple chiral centers making them inherently complex and challenging to prepare on a commercial scale. Improved methods for making such compounds would be advantageous.

SUMMARY

In some aspects, the present disclosure provides an amine compound represented by formula I:

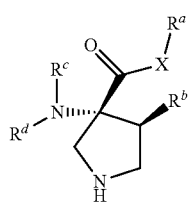

(I)

wherein the variables are defined herein. In specific aspects of the present disclosure, the amine compound has an enantiomeric excess (ee) of greater than 75% ee, greater than 80% ee, greater than 85% ee, greater than 90% ee, greater than 95% ee, greater than 97%% ee, greater than 98% ee or greater than 99% ee.

In another aspect, the present disclosure provides a salt of an amine compound represented by formula I and a carboxylic acid compound, such as that represented by formula A or formula B:

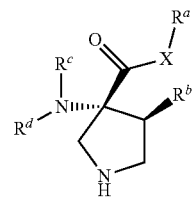

(I)

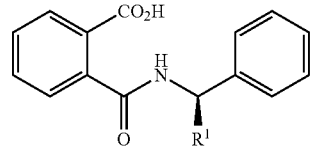

(A)

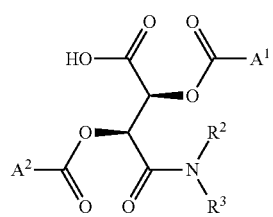

(B)

wherein the variables are defined herein.

In certain such embodiments, the disclosure provides crystals of such amine compounds, crystals of such salts of the amine compounds and compositions comprising such crystals, especially compositions and crystals in which the salt is enriched for one diastereomer (i.e., one enantiomer of the conjugate acid of the amine compound is present in excess over the other enantiomer, and the conjugate base of the carboxylic acid compound is present essentially as a single enantiomer (e.g., at least 98% ee)).

In some aspects, the present disclosure provides a method of preparing the salt by fractional crystallization from a solution, e.g., a solution comprising the amine compound (or its conjugate acid) and its enantiomer (e.g., in a racemic mixture or in less than 98% ee of the compound of formula I) and essentially a single enantiomer (e.g., at least 98% ee) of the carboxylic acid compound or its conjugate base. In some aspects, the present disclosure provides methods to prepare the chiral carboxylic acids used in the resolution process and methods to determine the enantiomeric excess of the resolved products using chiral HPLC.

The present disclosure also provides a synthetic process using the aforementioned amine compounds to prepare an arginase inhibitor of formula III:

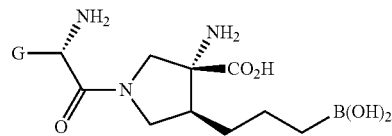

(III)

wherein the variable G is defined herein, and wherein a compound of formula I is an intermediate in the process. In particular embodiments, the compound of formula III has an ee of greater than 75% ee, greater than 80% ee, greater than 85% ee, greater than 90% ee, greater than 95% ee, greater than 97%% ee, greater than 98% ee or greater than 99% ee.

DETAILED DESCRIPTION

Figure 1:
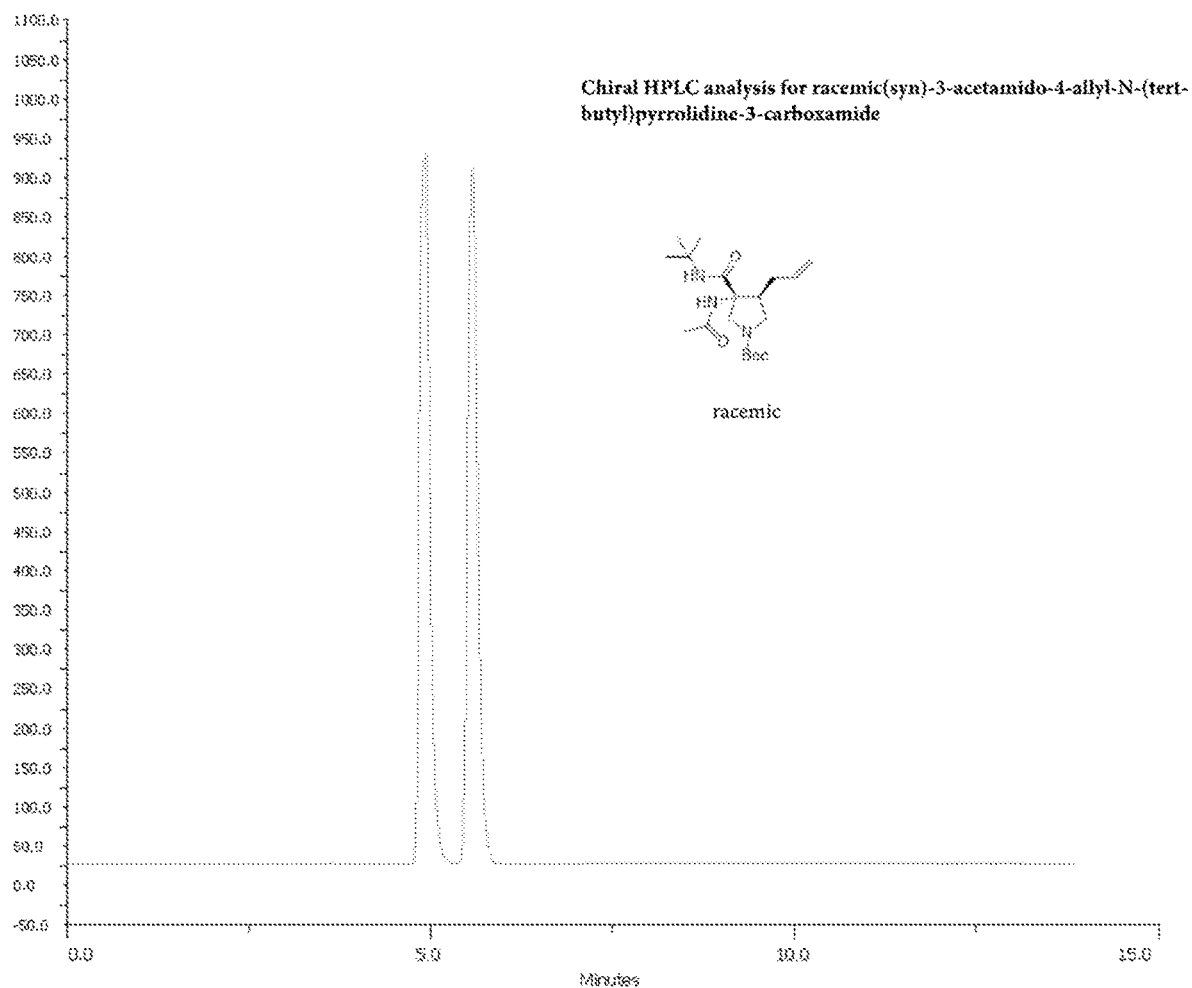
FIG. 1 shows the results of the chiral HPLC analysis for the racemic (syn)-3-acetamido-4-allyl-N-(tert-butyl)-pyrrolidine-3-carboxamide prepared in Example 1.

In some aspects, the present disclosure provides an amine compound represented by formula I:

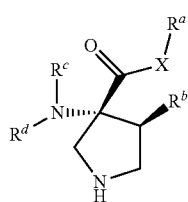
(I)

wherein:
X is O, S, or $NR^e$;
$R^a$ is H, lower alkyl, or lower cycloalkyl;
$R^b$ is —$CH_2CH=CH_2$, —$CH_2CH_2CH_2Z^1$, —$(CH_2)_nC(O)H$, or —$(CH_2)_nCO_2Z^2$;
$R^c$ and $R^d$ are independently H, lower alkyl, lower cycloalkyl, silyl, acyl, acyloxy; or $R^c$ and $R^d$, together with the N that links them, form an optionally substituted 3- to 6-membered heteroaryl or heterocyclic ring;
$R^e$ is H or lower alkyl, such as methyl;
n is 1 or 2;
$Z^1$ is a halogen, alkyl sulfonate, aryl sulfonate, or an alkyl sulfonate optionally substituted with one or more halogen atoms; and
$Z^2$ is H, lower alkyl, or lower cycloalkyl.

In some embodiments, the depicted amine compound of formula I has an enantiomeric excess of greater than 70% ee, 80% ee, 90% ee, 95% ee, 96% ee, 97% ee, 98% ee, 99% ee, or 99.5% ee. In other embodiments, the depicted amine compound has an enantiomeric excess of at least 90% ee, at least 95% ee, or even 98%, 99%, 99.5% or greater ee. In specific embodiments, the enantiomeric excess of the compound of formula I is bounded by any of the two foregoing embodiments, e.g., an ee ranging from 70% to 90%, from 80% to 90%, from 90% to 95%, from 80% to 99.5%, from 90% to 99.5%, from 95% to 99.5%, and so on, and so forth.

In some embodiments, $R^a$ is H, $C_{1-4}$ alkyl, or $C_{3-4}$ cycloalkyl. In some such embodiments, $R^a$ is H, methyl, ethyl, propyl, isopropyl, isobutyl, tert-butyl, cyclopropyl, or cyclobutyl. In some particular embodiments, $R^a$ is tert-butyl.

In some embodiments, $R^b$ is allyl, 3-fluoropropyl, 3-chloropropyl, 3-bromopropyl, 3-iodopropyl, 3-propane methanesulfonate, 3-propane trifluoromethanesulfonate, 3-propane benzenesulfonate, 3-propane para-tolylsulfonate, acetaldehyde, 3-propionaldehyde, acetic acid, 3-propanoic acid, methyl acetate, methyl 3-propanate, ethyl acetate, or ethyl 3-propanate. In some particular embodiments, $R^b$ is allyl.

In some embodiments, $R^c$ is H, $C_{1-4}$ alkyl, $C_{3-4}$ cycloalkyl. In some such embodiments, $R^c$ is H, methyl, ethyl, propyl, isopropyl, isobutyl, sec-butyl, tert-butyl, cyclopropyl, or cyclobutyl. In some particular embodiments, $R^c$ is H.

In some embodiments, $R^d$ is a silyl, acyl, or acyloxy group. In some such embodiments, $R^d$ is trimethylsilyl, triethylsilyl, triisopropylsilyl, tert-butyldimethylsilyl, formyl, acetyl, trifluoroacetyl, propionyl, butanoyl, isobutanoyl, tert-butanoyl, cyclopropanoyl, cyclobutanoyl, benzoyl, methyloxycarbonyl, ethyloxycarbonyl, isopropryloxycarbonyl, tert-butyloxycarbonyl, benzyloxycarbonyl, allyloxycarbonyl, or 9-fluorenylmethyloxycarbonyl. In some particular embodiments, $R^d$ is acetyl or trifluoroacetyl.

In some embodiments, $R^e$ and $R^d$, together with the N that links them, form a heterocyclic or heteroaryl ring. In some such embodiments, $R^e$ and $R^d$, together with the N that links them, form 2,5-dimethylpyrrole, 1H-pyrrole-2,5-dione, pyrrolidine-2,5-dione, or isoindoline-1,3-dione.

In some embodiments, X is O or S.

In some embodiments, X is $NR^e$. In some particular embodiments, $R^e$ is H.

In some particular embodiments, the amine compound is a compound of formula II:

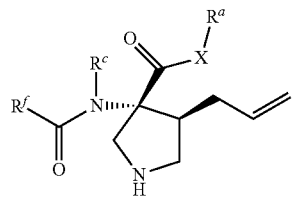
(II)

In some embodiments, the depicted amine compound of formula II has an enantiomeric excess of greater than 70% ee, 80% ee, 90% ee, 95% ee, 96% ee, 97% ee, 98% ee, 99% ee, or 99.5% ee. In other embodiments, the depicted amine compound has an enantiomeric excess of at least 90% ee, at least 95% ee, or even 98%, 99%, 99.5% or greater ee. In specific embodiments, the enantiomeric excess of the compound of formula II is bounded by any of the two foregoing embodiments, e.g., an ee ranging from 70%-90%, from 80%-90%, from 90% to 95%, from 80% to 99.5%, from 90% to 99.5%, from 95% to 99.5%, and so on, and so forth.

In some particular embodiments, the amine compound is a compound of formula IIa:

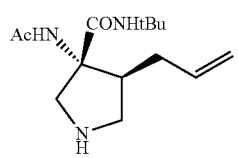
(IIa)

In some embodiments, the depicted amine compound of formula IIa has an enantiomeric excess of greater than 70% ee, 80% ee, 90% ee, 95% ee, 96% ee, 97% ee, 98% ee, 99% ee, or 99.5% ee. In other embodiments, the depicted amine compound has an enantiomeric excess of at least 90% ee, at least 95% ee, or even 98%, 99%, 99.5% or greater ee. In specific embodiments, the enantiomeric excess of the compound of formula IIa is bounded by any of the two foregoing embodiments, e.g., an ee ranging from 70% to 90%, from 80% to 90%, from 90% to 95%, from 80% to 99.5%, from 90% to 99.5%, from 95% to 99.5%, and so on, and so forth.

In some aspects, the present disclosure provides a salt of an amine compound represented by formula I and a carboxylic acid compound represented by formula A or B:

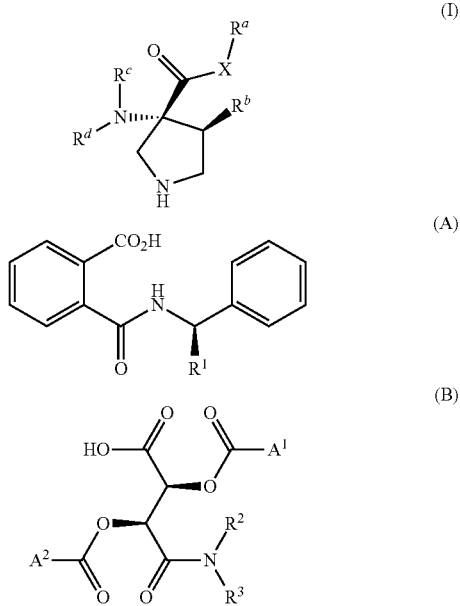

wherein:
X is O, S, or NR$^e$;
R$^a$ is H, lower alkyl, or lower cycloalkyl;
R$^b$ is —CH$_2$CH═CH$_2$, —(CH$_2$)$_n$CH$_2$Z$^1$, —(CH$_2$)$_n$C(O)H, or —(CH$_2$)$_n$CO$_2$Z$^2$;
R$^c$ and R$^d$ are independently H, lower alkyl, lower cycloalkyl, silyl, acyl, acyloxy; or R and R$^d$, together with the N that links them, form an optionally substituted 3- to 6-membered heteroaryl or heterocyclic ring;
R$^e$ is H or lower alkyl, such as methyl;
n is 1 or 2;
Z$^1$ is a halogen, alkyl sulfonate, aryl sulfonate, or an alkyl sulfonate optionally substituted with one or more halogen atoms;
Z$^2$ is H, lower alkyl, or lower cycloalkyl;
A$^1$ is phenyl or 5-6 membered heteroaryl, and is optionally substituted by up to 4 R$^4$;
A$^2$ is phenyl or 5-6 membered heteroaryl, and is optionally substituted by up to 4 R$^5$;
R$^1$ is lower alkyl or lower cycloalkyl;
R$^2$ and R$^3$ are independently H, lower alkyl, or lower cycloalkyl; or R$^2$ and R$^3$, together with the N that links them, form an optionally substituted 3- to 6-membered saturated heterocyclic ring optionally containing 1 or 2 additional heteroatoms selected from S and O; and R$^4$ and R$^5$ are independently halogen, hydroxyl, nitro, lower alkyl, or lower cycloalkyl.

In some embodiments, the salt is essentially a single enantiomer of a single diastereomer. In some embodiments, the amine compound in the salt is enantiomerically enriched in the depicted enantiomer, such as greater than 70% ee, 80% ee, 90% ee, 95% ee, 96% ee, 97% ee, 98% ee, 99% ee, or at least 99.5% ee.

In some embodiments, R$^a$ is H, C$_{1-4}$ alkyl, or C$_{3-4}$ cycloalkyl. In some such embodiments, R$^a$ is H, methyl, ethyl, propyl, isopropyl, isobutyl, tert-butyl, cyclopropyl, or cyclobutyl. In some particular embodiments, R$^a$ is tert-butyl.

In some embodiments, R$^b$ is allyl, 3-fluoropropyl, 3-chloropropyl, 3-bromopropyl, 3-iodopropyl, 3-propane methanesulfonate, 3-propane trifluoromethanesulfonate, 3-propane benzenesulfonate, 3-propane para-tolylsulfonate, acetaldehyde, 3-propionaldehyde, acetic acid, 3-propanoic acid, methyl acetate, methyl 3-propanate, ethyl acetate, or ethyl 3-propanate. In some particular embodiments, R$^b$ is allyl.

In some embodiments, R$^c$ is H, C$_{1-4}$ alkyl, or C$_{3-4}$ cycloalkyl. In some such embodiments, R$^c$ is H, methyl, ethyl, propyl, isopropyl, isobutyl, sec-butyl, tert-butyl, cyclopropyl, or cyclobutyl. In some particular embodiments, R$^c$ is H.

In some embodiments, R$^d$ is a silyl, acyl, or acyloxy group. In some such embodiments, R$^d$ is trimethylsilyl, triethylsilyl, triisopropylsilyl, tert-butyldimethylsilyl, formyl, acetyl, trifluoroacetyl, propionyl, butanoyl, isobutanoyl, tert-butanoyl, cyclopropanoyl, cyclobutanoyl, benzoyl, methyloxycarbonyl, ethyloxycarbonyl, isopropryloxycarbonyl, tert-butyloxycarbonyl, benzyloxycarbonyl, allyloxycarbonyl, or 9-fluorenylmethyloxycarbonyl. In some particular embodiments, R$^d$ is acetyl or trifluoroacetyl.

In some embodiments, R and R$^d$, together with the N that links them, form a heterocyclic or heteroaryl ring. In some such embodiments, R$^c$ and R$^d$, together with the N that links them, form 2,5-dimethylpyrrole, 1H-pyrrole-2,5-dione, pyrrolidine-2,5-dione, or isoindoline-1,3-dione.

In some embodiments, X is O or S.

In some embodiments, X is NR$^e$. In some particular embodiments, R$^e$ is H.

In some aspects, the present disclosure provides a salt of an amine compound represented by formula II and a carboxylic acid compound represented by formula A or B:

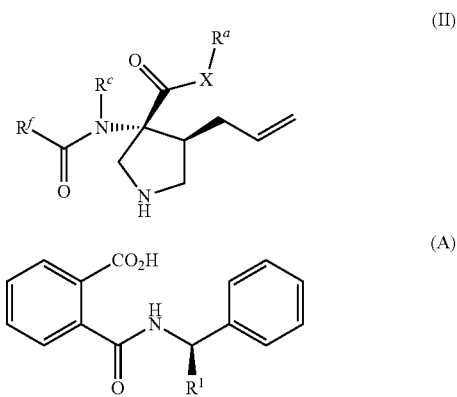

(B)

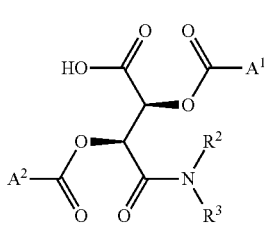

wherein:
A¹ is phenyl or 5-6 membered heteroaryl, and is optionally substituted by up to 4 $R^4$;
A² is phenyl or 5-6 membered heteroaryl, and is optionally substituted by up to 4 $R^5$;
X is O, S, or $NR^e$;
$R^a$, $R^c$, and $R^f$ are independently H, lower alkyl, or lower cycloalkyl;
$R^e$ is H or lower alkyl, such as methyl;
$R^1$ is lower alkyl or lower cycloalkyl;
$R^2$ and $R^3$ are H, lower alkyl, or lower cycloalkyl; or $R^2$ and $R^3$, together with the N that links them, form an optionally substituted 3- to 6-membered saturated heterocyclic ring optionally containing 1 or 2 additional heteroatoms selected from S and O; and
$R^4$ and $R^5$ are independently halogen, hydroxyl, nitro, lower alkyl, or lower cycloalkyl.

In some embodiments, $R^a$ is H, $C_{1-4}$ alkyl, or $C_{3-4}$ cycloalkyl. In some such embodiments, $R^a$ is H, methyl, ethyl, propyl, isopropyl, isobutyl, sec-butyl, tert-butyl, cyclopropyl, or cyclobutyl. In some particular embodiments, $R^a$ is tert-butyl.

In some embodiments, $R^c$ is H, $C_{1-4}$ alkyl, or $C_{3-4}$ cycloalkyl. In some such embodiments, $R^c$ is H, methyl, ethyl, propyl, isopropyl, isobutyl, sec-butyl, tert-butyl, cyclopropyl, or cyclobutyl. In some particular embodiments, $R^c$ is H.

In some embodiments, $R^b$ is H, $C_{1-4}$ alkyl, or $C_{3-4}$ cycloalkyl. In some such embodiments, $R^f$ is H, methyl, ethyl, propyl, isopropyl, isobutyl, sec-butyl, tert-butyl, cyclopropyl, or cyclobutyl. In some particular embodiments, $R^f$ is methyl.

In some embodiments, X is O or S.

In some embodiments, X is $NR^d$. In some particular embodiments, $R^d$ is H.

In some particular embodiments, the amine potion of the salt is a compound of formula (IIa).

In some embodiments, the salt is essentially a single enantiomer of a single diastereomer. In some embodiments, the amine compound in the salt is enantiomerically enriched in the depicted enantiomer, such as greater than 70% ee, 80% ee, 90% ee, 95% ee, 96% ee, 97% ee, 98% ee, 99% ee, or at least 99.5% ee. In some embodiments, the carboxylic acid compound in the salt is enantiomerically enriched in the depicted enantiomer, such as at least 90% ee, at least 95% ee, or even 98%, 99% or greater ee.

In some embodiments, A¹ is phenyl. In some embodiments, A¹ is 5-6 membered heteroaryl, such as thiophenyl, furanyl, thiazolyl, isothiazolyl, indazolyl, oxazolyl, isoxazolyl, pyridazinyl, pyrimidyl, pyrazinyl, 1,2,4-triazinyl, 1,2,3-triazinyl, or 1,3,5-triazinyl.

In some embodiments, A² is phenyl. In some embodiments, A² is 5-6 membered heteroaryl, such as thiophenyl, furanyl, thiazolyl, isothiazolyl, indazolyl, oxazolyl, isoxazolyl, pyridazinyl, pyrimidyl, pyrazinyl, 1,2,4-triazinyl, 1,2,3-triazinyl, or 1,3,5-triazinyl.

In some embodiments, A¹ and A² are identical. In some embodiments, A¹ and A² are different.

In some embodiments, A¹ and A² are both phenyl.

In some embodiments, A¹ is substituted by one $R^4$, for example at the 2-, 3-, 4-, or 5-position relative to the point of attachment to the remainder of formula B.

In some embodiments, A² is substituted by one $R^5$, for example at the 2-, 3-, 4-, or 5-position relative to the point of attachment to the remainder of formula B.

In some embodiments, A¹ is substituted by two $R^4$, for example at the 1,2-; 2,3-; 1,3-; 1,4-; 1,5-; or 2,4-positions relative to the point of attachment to the remainder of formula B.

In some embodiments, A² is substituted by two $R^5$, for example at the 1,2-; 2,3-; 1,3-; 1,4-; 1,5-; or 2,4-positions relative to the point of attachment to the remainder of formula B.

In some embodiments, A¹ and A² are identically substituted. In some embodiments, A¹ and A² are differently substituted.

In some embodiments, the carboxylic acid compound is represented by formula A or formula B-I:

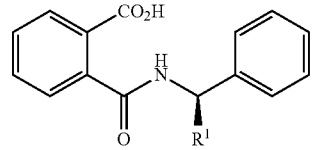

(A)

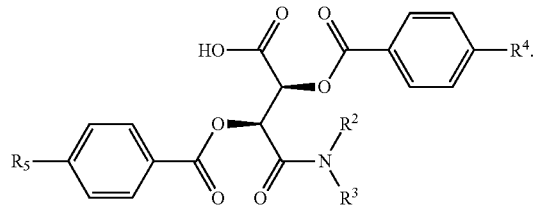

(B-I)

In some embodiments, the carboxylic acid compound is represented by formula A. In some embodiments, $R^1$ is H, $C_{1-4}$ alkyl, or $C_{3-4}$ cycloalkyl. In some embodiments, $R^1$ is methyl, ethyl, propyl, isopropyl, isobutyl, sec-butyl, tert-butyl, cyclopropyl, or cyclobutyl. In some particular embodiments, $R^1$ is methyl.

In some embodiments, the carboxylic acid compound is represented by formula B. In some particular embodiments, the carboxylic acid compound is represented by formula B-I.

In some embodiments, $R^2$ and $R^3$ are independently H, $C_{1-4}$ alkyl, or $C_{3-4}$ cycloalkyl; or $R^2$ and $R^3$, together with the N that links them, form an N-linked 3- to 6-membered saturated heterocyclic ring. In some particular embodiments, $R^2$ and $R^3$ are independently methyl, ethyl, or isopropyl; or $R^2$ and $R^3$, together with the N that links them, form a pyrrolidinyl.

In some embodiments, $R^4$ is $C_{1-4}$ alkyl, or $C_{3-4}$ cycloalkyl. In some embodiments, $R^4$ is methyl, ethyl, propyl, isopropyl, isobutyl, sec-butyl, tert-butyl, cyclopropyl, or cyclobutyl. In some particular embodiments, $R^4$ is methyl. In other embodiments, $R^4$ is halogen, hydroxyl, or nitro. In certain particular embodiments, $R^4$ and $R^5$ are the same.

In some embodiments, $R^5$ is $C_{1-4}$ alkyl, or $C_{3-4}$ cycloalkyl. In some embodiments, $R^5$ is H, methyl, ethyl, propyl, isopropyl, isobutyl, sec-butyl, tert-butyl, cyclopropyl, or cyclobutyl. In some particular embodiments, $R^5$ is methyl. In other embodiments, $R^5$ is halogen, hydroxyl, or nitro.

In some particular embodiments, the carboxylic acid compound is:

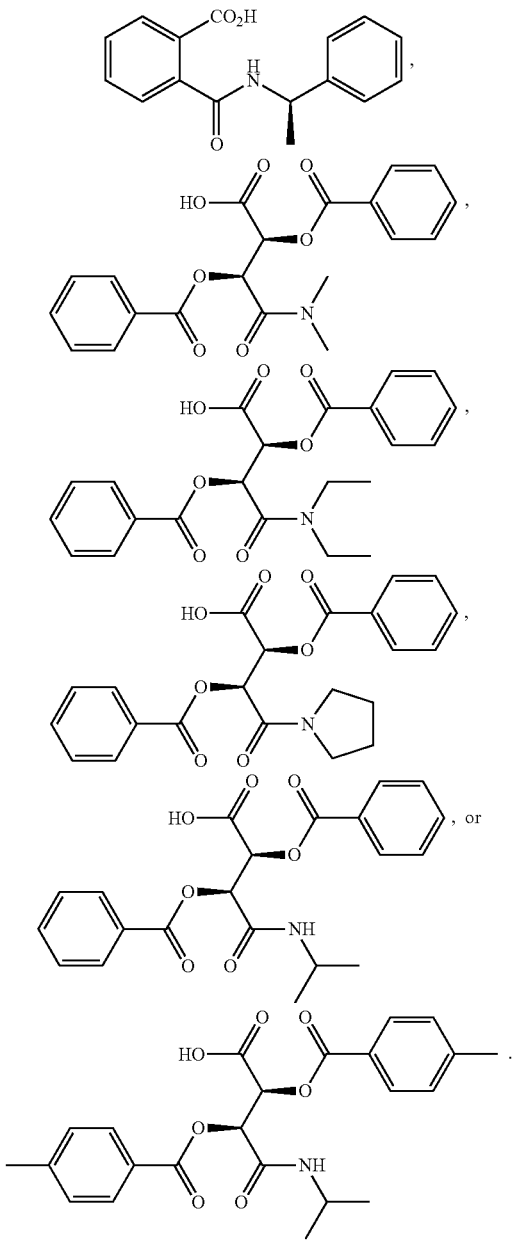

In some aspects, the present disclosure provides a method of preparing the salts provided herein by fractional crystallization from a solution, comprising: preparing a crystallization solution comprising the amine compound, essentially a single enantiomer of the carboxylic acid compound, and a solvent; and crystallizing from the crystallization solution a salt of the amine compound and the carboxylic acid compound.

In some embodiments, the solvent comprises water, methanol, ethanol, isopropanol, ethyl acetate, or acetonitrile or a mixture of any of these. In some embodiments, the solvent is isopropanol. In some embodiments, the solvent is ethyl acetate. In some embodiments, the solvent is acetonitrile. In some embodiments, the solvent is a mixture of methanol and ethyl acetate, such as 5-35% methanol/ethyl acetate, preferably 15-25% methanol/ethyl acetate. In some embodiments, the solvent is a mixture of methanol and isopropanol, such as 5-35% methanol/isopropanol, preferably 5-25% methanol/isopropanol. In some embodiments, the solvent is methanol.

In some embodiments, the crystallization solution comprises the amine compound and its enantiomer. In some embodiments, the crystallization solution comprises a racemic mixture of the amine compound and its enantiomer. In some embodiments, the crystallization solution comprises an enantiomeric excess of the amine compound over its enantiomer. In some such embodiments, the amine compound in the crystallization solution is present at less than 5% ee, less than 10% ee, less than 15% ee, less than 20% ee, less than 25% ee, less than 30% ee, less than 40% ee, less than 50% ee, less than 60% ee, less than 70% ee, less than 80% ee, less than 90% ee, less than 95% ee, at least 96% ee, at least 97% ee, at least 98% ee, at least 99% ee, or at least 99.5% ee. In some embodiments, the enantiomer of the amine compound is enriched for one enantiomer. In some such embodiments, the enantiomer of the amine compound in the crystallization solution has at least 5% ee, at least 10% ee, at least 15% ee, at least 20% ee, at least 25% ee, at least 30% ee, at least 40% ee, at least 50% ee, at least 60% ee, at least 70% ee, at least 80% ee, at least 90% ee, at least 95% ee, at least 96% ee, at least 97% ee, at least 98% ee, at least 99% ee, or at least 99.5% ee.

In some embodiments, the salt of the amine compound with the carboxylic acid that results from the crystallizing step is essentially a single enantiomer of a single diastereomer. In some embodiments, the salt is present in at least 5% ee, at least 10% ee, at least 15% ee, at least 20% ee, at least 25% ee, at least 30% ee, at least 40% ee, at least 50% ee, at least 60% ee, at least 70% ee, at least 80% ee, at least 90% ee, at least 95% ee, at least 96% ee, at least 97% ee, at least 98% ee, at least 99% ee, or at least 99.5% ee.

In some embodiments, before the desired amine compound is crystallized, the undesired enantiomer is first crystallized using an enantiomer of one of the carboxylic acid compounds. By performing this pre-crystallization step, the crystallization solution is formed as the supernatant, and is thereby enriched in the desired amine compound relative to the starting solution. Thus, according to certain embodiments, preparing the crystallization solution comprises preparing a precursor solution comprising the amine compound, a second, undesired, enantiomer of the amine compound, and a second enantiomer of the carboxylic acid compound. That is, the precursor solution comprises the enantiomeric amines of formulas II and II', and the carboxylic acid of either formula A', B', or B-I' (i.e., the carboxylic acid is the opposite enantiomer from that of formula A, B, or B-I):

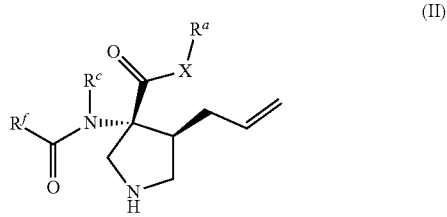

(II)

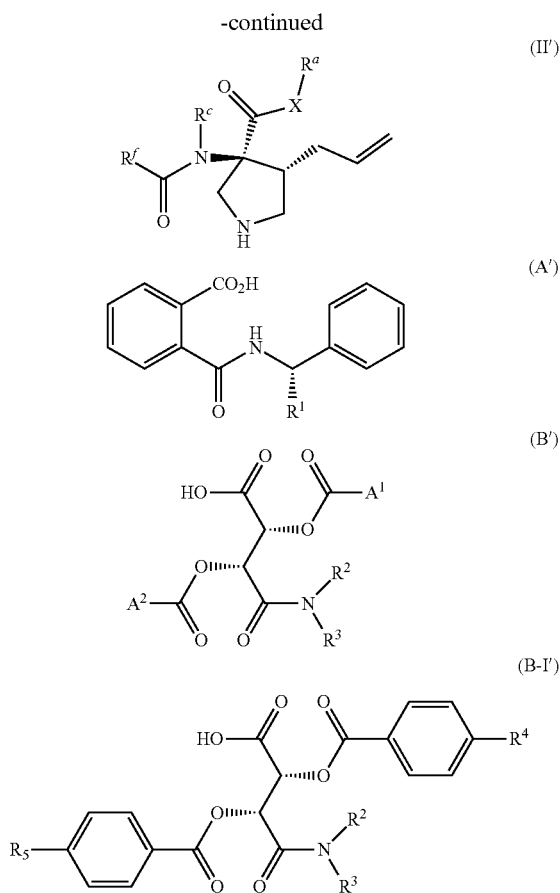

The variables in formulas II, II', A', and B' may be selected as defined above with respect to formulas II, A, and B. According to these embodiments, the second enantiomer of the carboxylic acid compound (i.e., the enantiomer depicted in formula A', B', or B-I') is selected to crystallize with the undesired enantiomer of the amine compound (i.e., the enantiomer depicted in formula II'). Next, the salt of the second enantiomer of the amine compound with the second enantiomer of the carboxylic acid compound is crystallized from the precursor solution, thereby forming the crystallization solution as the supernatant. It is not necessary that the carboxylic acid used in the pre-crystallization step (i.e., the enantiomer depicted in formula A', B', or B-I') is the opposite enantiomer of the carboxylic acid used in the crystallization step (i.e., the enantiomer depicted in formula A, B, or B-I). In some embodiments, the carboxylic acid used in the pre-crystallization step is the opposite enantiomer of the carboxylic acid used in the crystallization step. In some embodiments, the carboxylic acid used in the pre-crystallization step is not a stereoisomer of the carboxylic acid used in the crystallization step.

Crystallizing the undesired enantiomer in this way can result in a crystallization solution in which the desired amine compound is present in at least 5% ee, at least 10% ee, at least 15% ee, at least 20% ee, at least 25% ee, at least 30% ee, at least 40% ee, at least 50% ee, at least 60% ee, at least 70% ee, at least 80% ee, at least 90% ee, at least 95% ee, at least 96% ee, at least 97% ee, at least 98% ee, at least 99% ee, or at least 99.5% ee. The desired salt can then be crystallized from the crystallization solution as described above.

In some embodiments, the present disclosure provides a method for separating a mixture of (3R,4S)-3-acetamido-4-allyl-N-(tert-butyl)pyrrolidine-3-carboxamide IIa and (3S,4R)-3-acetamido-4-allyl-N-(tert-butyl)pyrrolidine-3-carboxamide IIb into essentially single enantiomers using selective crystallization with chiral carboxylic acids according to formula A or B. Such carboxylic acids are commercially available or may be prepared in one or two synthetic steps from phthalic anhydride and diacylated tartaric acid or its anhydride, such as (+)-2,3-dibenzoyl-D-tartaric acid, (−)-2,3-dibenzoyl-L-tartaric acid, (+)-O,O'-di-p-toluoyl-D-tartaric acid or (−)-O,O'-di-p-toluoyl-L-tartaric acid.

In a typical procedure, an amine compound such as (3R,4S)-3-acetamido-4-allyl-N-(tert-butyl)pyrrolidine-3-carboxamide IIa and its enantiomer (3S,4R)-3-acetamido-4-allyl-N-(tert-butyl)pyrrolidine-3-carboxamide IIb is dissolved in a suitable solvent or solvent mixture and combined with a second solution containing essentially a single enantiomer of a selected carboxylic acid of formula A or formula B. The amine compound IIa may be present as a racemic mixture with its enantiomer IIb, it may be enriched over IIb, or IIb may be enriched over IIa. In some embodiments, IIa is enriched to 5% ee, 10% ee, 15% ee, 20% ee, 25% ee, 30% ee, 40% ee, 50% ee, 60% ee, 70% ee, 80% ee, 90% ee, or even 95% or greater ee. In some embodiments, IIb is enriched to 5% ee, 10% ee, 15% ee, 20% ee, 25% ee, 30% ee, 40% ee, 50% ee, 60% ee, 70% ee, 80% ee, 90% ee, or even 95% or greater ee. The solvents that may be used alone or in combination as solvent mixtures include but are not limited to water, methanol, ethanol, isopropyl alcohol, acetonitrile and ethyl acetate. In some cases, warming one or both of the solutions may be required to fully dissolve the amine or the carboxylic acid. Once the solutions are combined, the resulting solution is allowed to stand until the salt formed from the chiral carboxylic acid and substantially one of the amine enantiomers forms a precipitate, the selective crystallization.

The time required for this crystallization process will vary depending on the specific carboxylic acid, solvents, concentration, and temperature. In some instances, the precipitate will begin forming in minutes, in others in may take several hours or even days. In general, a slower process will give better enantiomeric selectivity. Thus in some instances, crystallization conditions that give a slower process are preferable. These include more polar solvents, less concentrated solutions and higher temperatures or a slow rate of cooling.

Since the methods described herein use chiral carboxylic acids that are readily available (commercially or in a few synthetic steps) in either enantiomeric form, either enantiomer of the amine can be obtained simply by using the appropriate enantiomer of the carboxylic acid.

In some cases, a greater yield and/or enantiomeric excess can be obtained by using two sequential crystallizations—the first with one enantiomer of the carboxylic acid to remove a significant portion of the undesired amine (undesired enantiomer) as the precipitated salt, then a second crystallization with the second enantiomer of the carboxylic acid to obtain the desired amine as the precipitated salt.

Although numerous carboxylic acids of formula A and formula B may be used as disclosed herein, certain particular carboxylic acids include those illustrated and named below as compounds 3-8 in Table 1.

| Compound | Structure | Name |
|---|---|---|
| 3 | 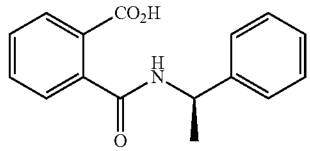 [SMILES: C[C@@H](NC(=O)c1ccccc1C(=O)O)c1ccccc1] | (R)-2-((1-phenylethyl)carbamoyl)benzoic acid |
| 4 | 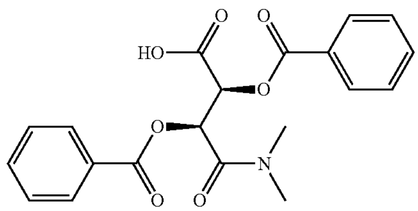 [SMILES: CN(C)C(=O)[C@@H](OC(=O)c1ccccc1)[C@H](OC(=O)c1ccccc1)C(=O)O] | (2S,3S)-2,3-bis(benzoyloxy)-4-(dimethylamino)-4-oxobutanoic acid |
| 5 | 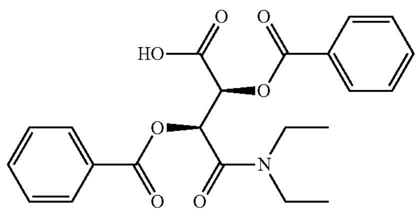 [SMILES: CCN(CC)C(=O)[C@@H](OC(=O)c1ccccc1)[C@H](OC(=O)c1ccccc1)C(=O)O] | (2S,3S)-2,3-bis(benzoyloxy)-4-(diethylamino)-4-oxobutanoic acid |
| 6 | 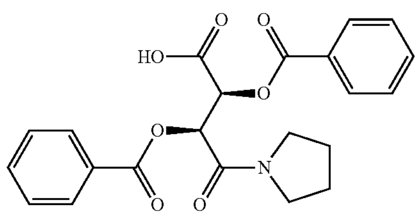 [SMILES: O=C(O[C@H](C(=O)O)[C@H](OC(=O)c1ccccc1)C(=O)N1CCCC1)c1ccccc1] | (2S,3S)-2,3-bis(benzoyloxy)-4-oxo-4-(pyrrolidin-1-yl)butanoic acid |
| 7 | 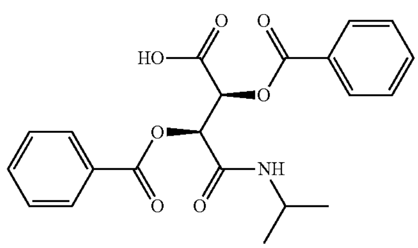 [SMILES: CC(C)NC(=O)[C@@H](OC(=O)c1ccccc1)[C@H](OC(=O)c1ccccc1)C(=O)O] | (2S,3S)-2,3-bis(benzoyloxy)-4-(isopropylamino)-4-oxobutanoic acid |
| 8 | 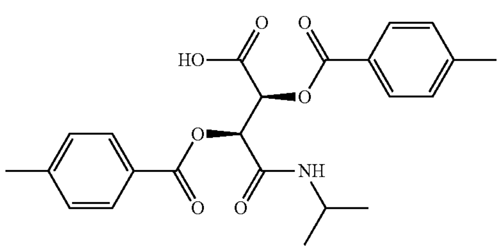 | (3S,4S)-5-(isopropylamino)-3,4-bis((4-methylbenzoyl)oxy)-2,5-dioxopentanoic acid |

The starting materials and reagents used in the preparation of the compounds in the present disclosure are either available from commercial suppliers such as Sigma-Aldrich (St. Louis, Mo.) or Fisher Scientific (Hampton, N.H.) or are prepared by methods known to those skilled in the art following procedures set forth in references such as Fieser and Fieser's Reagents for Organic Synthesis, Volumes 1-17 (John Wiley and Sons, 1991), Organic Reactions, Volumes 1-40 (John Wiley and Sons, 1991), and March's Advanced Organic Chemistry (John Wiley and Sons, 4$^{th}$ Edition). The schemes provided herein are merely illustrative of some methods by which the compounds of the present disclosure can be synthesized, and various modifications of these schemes can be made and suggested by those skilled in the art having referred to this disclosure. The starting materials, intermediates, and final products of the reaction may be isolated and purified using conventional techniques, including but not limited to filtration, distillation, crystallization, chromatography and the like.

The present disclosure also provides a synthetic process to prepare an arginase inhibitor of formula III:

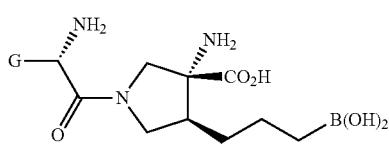

(III)

wherein G of arginase inhibitor III is an amino acid side chain, such as hydrogen (glycine), methyl (alanine), isopropyl (valine), sec-butyl (isoleucine), —CH$_2$CH(CH$_3$)$_2$(leucine), benzyl (phenylalanine), p-hydroxybenzyl (tyrosine), —CH$_2$OH (serine), —CH(OH)CH$_3$ (threonine), —CH$_2$-3-indoyl (tryptophan), —CH$_2$COOH (aspartic acid), —CH$_2$CH$_2$COOH (glutamic acid), —CH$_2$C(O)NH$_2$ (asparagine), —CH$_2$CH$_2$C(O)NH$_2$ (glutamine), —CH$_2$SH (cysteine), —CH$_2$CH$_2$SCH$_3$ (methionine), —(CH$_2$)$_4$NH$_2$ (lysine), —(CH$_2$)$_3$NHC(=NH)NH$_2$ (arginine) or —CH$_2$-3-imidazoyl (histidine).

In particular embodiments, G is methyl. In other particular embodiments, G is hydrogen. In other particular embodiments, G is —CH$_2$OH.

In particular embodiments, the compound of formula III obtained by the processes described here has an enantiomeric excess of greater than 80%, 90% ee, 95% ee, 96% ee, 97% ee, 98% ee, 99% ee, or even greater than 99.5% ee.

In accordance with the disclosure, the arginase inhibitor of general formula III can be prepared by using a compound of formula I, formula II or formula IIa as an intermediate. A general schematic for synthesizing a compound of formula III from a compound of formula I is depicted in Scheme A. In Scheme A, the multiple arrows represent multiple synthetic steps, which will be described in more detail below.

Scheme A

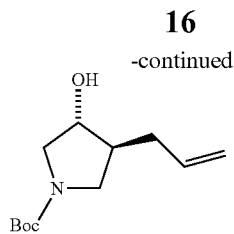

In some aspects, arginase inhibitors of general formula III can be prepared as illustrated and described in the general Scheme B below.

Scheme B

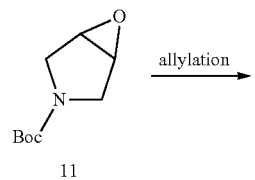

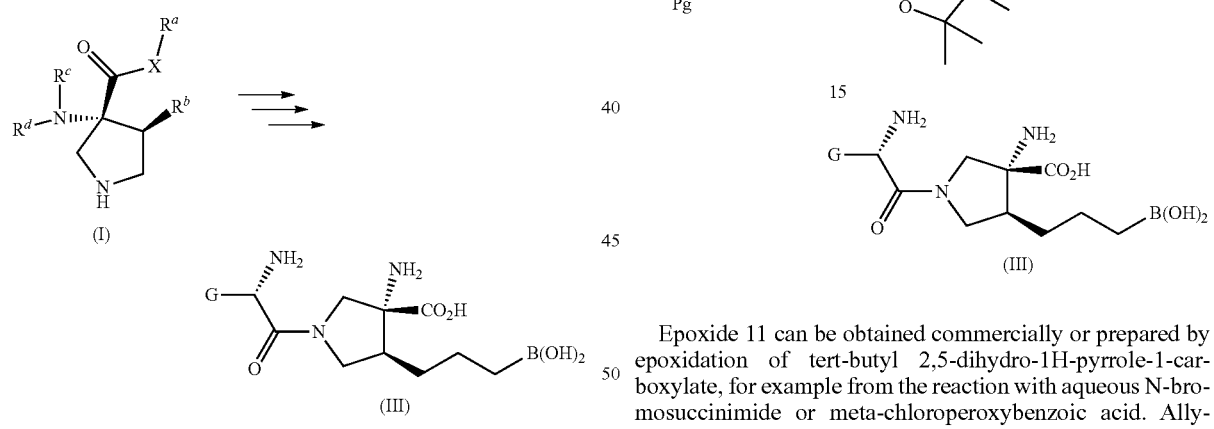

Epoxide 11 can be obtained commercially or prepared by epoxidation of tert-butyl 2,5-dihydro-1H-pyrrole-1-carboxylate, for example from the reaction with aqueous N-bromosuccinimide or meta-chloroperoxybenzoic acid. Allylation of epoxide 11 to form racemic alcohol 12 can be accomplished using an appropriate allyl metal nucleophile, such as an allyl lithium reagent, an ally magnesium reagent, an allyl zinc reagent, an allyl copper reagent, or reagents including mixtures of these metals. The epoxide ring opening may also be assisted with Lewis acids or transitional metals. Solvents can include any of those suitable for nucleophilic addition, such as but limited to diethyl ether, tetrahydrofuran, 2-methyltetrahydrofuran, and the like. Racemic alcohol 12 can then be oxidized to ketone 13 using known methods readily apparent to those skill in the art for secondary alcohols, such as but not limited to, Swern oxidation, Parikh-Doering oxidation, Corey-Kim oxidation, oxidation using hypervalent iodine, and the like. Ketone 13 can then be transformed in a multi-component reaction to racemic amino acid derivative 14. Such multi-component reactions can include but are not limited to, the Ugi reaction, the Strecker reaction, and variations thereof. Variations of solvent, addition sequences, and additives may also be employed in these reactions, for example the Ugi reaction can be performed in range of solvents such as but not limited to, trifluoroethanol, methanol, water, acetonitrile, dichloromethane, tetrahydrofuran, and mixtures thereof, and include additives such as ammonium hydroxide. Racemic amino acid derivation 14 can then be deprotected under readily available conditions (e.g., removal of Boc with TFA, HCl, or a Lewis acid), treated with DOWEX-550 hydroxide resin or slurried in an appropriate solvent (e.g., methyl tert-butyl ether) and filtered, to afford racemic amine (enantiomer IIa and enantiomer IIb). The racemic amine (IIa and IIb) can then be resolved according to the methods of the present disclosure to obtain chiral amine IIa. In some aspects, neutralization of the formed salt, for example using a base such as sodium bicarbonate, sodium carbonate, potassium bicarbonate, sodium methoxide, etc., can liberate the free amine from the salt to allow isolation of chiral amine IIa. Protection of chiral amine IIa and subsequent hydroboration can produce pinacol borate 15. In compound 15, Pg is a protecting group, as defined below. In other aspects before hydroboration, neutralization and protection can be performed in a single step using aqueous sodium bicarbonate and di-tert-butyl dicarbonate. The protected chiral amine can be subjected to further enantio-enrichment steps, such as by warm slurry in ethyl acetate and n-heptane mixtures and filtration after cooling. Hydroboration can be accomplished using known methods readily apparent to those skill in the art, such as using pinacol borane or bis(pinacolato)diboron in the present of an appropriate iridium or rhodium catalyst. A subsequent selective deprotection/amidation sequence followed by global deprotection can afford arginase inhibitor represented by formula III.

In certain aspects, the compounds of the present disclosure can be prepared using the methods illustrated in Schemes C and D below, and in the more detailed procedures described in the examples section. Racemic tert-butyl-trans-3-allyl-4-hydroxypyrrolidine-1-carboxylate (IIa and IIb) is prepared from commercially available epoxide 11 in four steps as outlined in Scheme C. Addition of allyl magnesium bromide in diethyl ether at 0° C. gives racemic alcohol 12, which after oxidation with sulfur trioxide pyridine complex and DMSO gives the corresponding ketone 13. Subsequent treatment with ammonium acetate and tert-butyl isocyanide in methanol at 0° C. gives the racemic amino acid derivative 14 as a mixture of syn- and anti-isomers which are separated by crystallization. Deprotection of the tert-butyl carbamate (Boc group) using trifluoroacetic acid in dichloromethane followed by treatment with DOWEX-550 hydroxide resin gives racemic amine (IIa and IIb) as a free base.

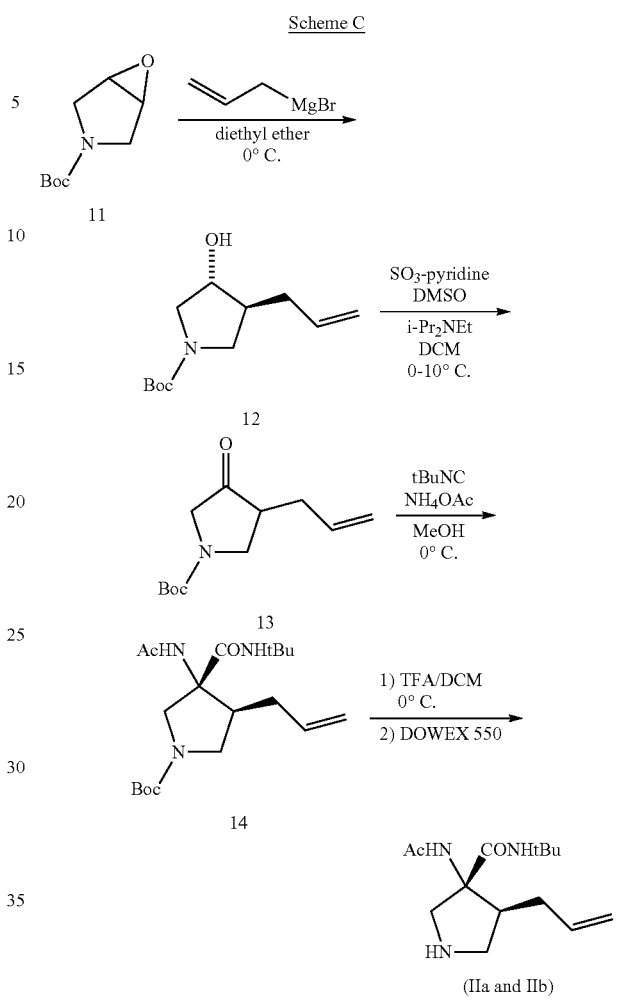

The method for resolving the racemic amine (IIa and IIb) into its substantially single enantiomers using a chiral carboxylic acid of the disclosure is illustrated in Scheme D. In this example, racemic (syn)-3-acetamido-4-allyl-N-(tert-butyl)pyrrolidine-3-carboxamide (IIa and IIb) and (R)-2-((1-phenylethyl)carbamoyl)benzoic acid 3 are dissolved in methanol (15%) and ethyl acetate (85%) with warming. Once the solution becomes clear, it is allowed to cool and a precipitate slowly forms. The precipitate, which is the salt formed from acid 3, and amine IIa, is separated by filtration. This salt can be free-based using standard methods or used directly in the next step of the synthesis.

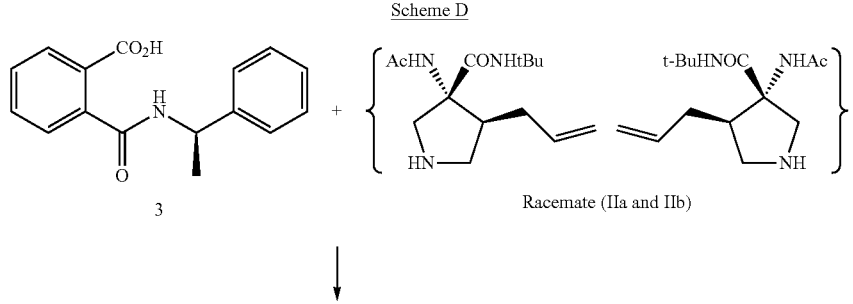

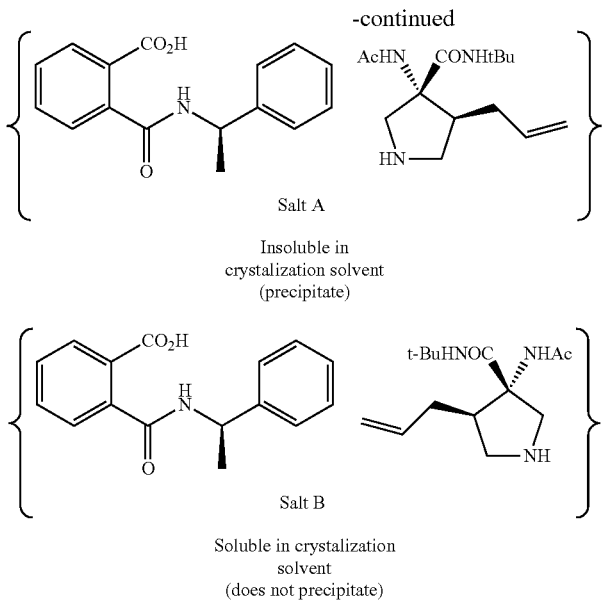

Salt A

Insoluble in crystalization solvent
(precipitate)

Salt B

Soluble in crystalization solvent
(does not precipitate)

The methods disclosed herein can be carried out by those generally skilled in the art of organic synthesis using the detailed experimental methods provided herein. It is understood that the process of selective crystallization is dependent on many factors including the choice of solvent(s), temperature, concentration and the amount of the chiral carboxylic acid present. The specific choice of these variables will determine the results of the crystallization and may be modified depending on the desired outcome (yield, enantiomeric excess, concentration, time, cost). For example, a more dilute crystallization solution will typically facilitate slower crystallization, often improving enantioselectivity, but with lower recovery; while a more concentrated solution will often accelerate the crystallization process, providing a higher yield but with a somewhat lower enantiomeric excess. Seed crystals of the desired material also will generally facilitate the crystallization process.

DEFINITIONS

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, trifluoromethoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10, more preferably from 1 to about 6 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen (e.g., fluoro), a hydroxyl, an alkoxy, a cyano, a nitro, an azido, a sulfhydryl, an alkylthio, a heterocyclyl, an aralkyl, or an aromatic or heteroaromatic moiety. In particular embodiments, the substituents on substituted alkyls are selected from $C_{1-6}$ alkyl, $C_{3-6}$ cycloalkyl, halogen, cyano, or hydroxyl. In more particular embodiments, the substituents on substituted alkyls are selected from fluoro, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of azido, imino, as well as ethers, alkylthios, —$CF_3$, —CN and the like. Exemplary substituted alkyls are described below. Cycloalkyls can be further substituted with alkyls, alkenyls, alkoxys, alkylthios, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups. Particular haloalkyl groups include trifluoromethyl, difluoromethyl, 2,2,2-trifluoroethyl, and pentafluoroethyl. $C_0$ alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

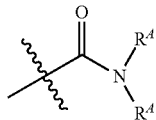

wherein each $R^A$ independently represent a hydrogen or hydrocarbyl group, or two $R^A$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

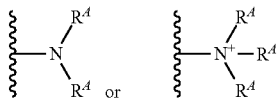

wherein each $R^A$ independently represents a hydrogen or a hydrocarbyl group, or two $R^A$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 6- or 10-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

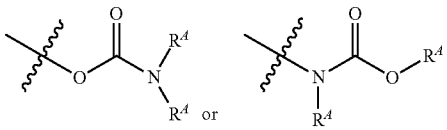

wherein each $R^A$ independently represent hydrogen or a hydrocarbyl group, such as an alkyl group, or both $R^A$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 3-8 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated, and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated, and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^A$, wherein R$^A$ represents a hydrocarbyl group.

The term "carboxy", as used herein, refers to a group represented by the formula —CO$_2$H.

The term "ester", as used herein, refers to a group —C(O)OR$^A$ wherein R$^A$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Particular heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, tetrahydropyran, tetrahydrofuran, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, alkoxy, or cycloalkyl is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, an alkoxy, a cyano, a nitro, an azido, a sulfhydryl, an alkylthio, a heterocyclyl, an aralkyl, or an aromatic or heteroaromatic moiety. In particular embodiments, the substituents on substituted alkyls are selected from $C_{1-6}$ alkyl, $C_{3-6}$ cycloalkyl, halogen, cyano, or hydroxyl. In more particular embodiments, the substituents on substituted alkyls are selected from fluoro, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO₃H, or a pharmaceutically acceptable salt thereof.

The term "sulfonamide" is art-recognized and refers to the group represented by the general formulae

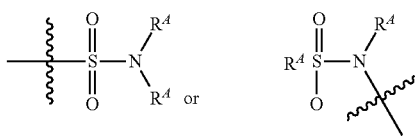

wherein each $R^A$ independently represents hydrogen or hydrocarbyl, such as alkyl, or both $R^A$ taken together with the intervening atom(s) complete a heterocycle having from 4 to 8 atoms in the ring structure.

The term "sulfoxide" is art-recognized and refers to the group —S(O)—$R^A$, wherein $R^A$ represents a hydrocarbyl.

The term "sulfonate" is art-recognized and refers to the group SO₃H, or a pharmaceutically acceptable salt thereof.

The term "sulfone" is art-recognized and refers to the group —S(O)₂—$R^A$, wherein $R^A$ represents a hydrocarbyl.

The term "thioalkyl", as used herein, refers to an alkyl group substituted with a thiol group.

The term "thioester", as used herein, refers to a group —C(O)S$R^A$ or —SC(O)$R^A$ wherein $R^A$ represents a hydrocarbyl.

The term "thioether", as used herein, is equivalent to an ether, wherein the oxygen is replaced with a sulfur.

The term "urea" is art-recognized and may be represented by the general formula

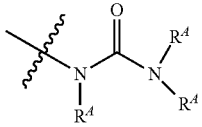

wherein each $R^A$ independently represents hydrogen or a hydrocarbyl, such as alkyl, or any occurrence of $R^A$ taken together with another and the intervening atom(s) complete a heterocycle having from 4 to 8 atoms in the ring structure.

"Protecting group" ("Pg") refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups (Pg) include, but are not limited to, formyl, acetyl, trifluoroacetyl, benzyl, methoxymethyl ("MOM"), benzyloxycarbonyl ("CBZ"), tert-butoxycarbonyl ("Boc"), trimethylsilyl ("TMS"), 2-trimethylsilyl-ethanesulfonyl ("2-TES"), triethylsilyl ("TES"), triisopropylsilyl ("TIPS"), tert-butyldimethylsilyltrityl ("TBDMS") and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "essentially a single enantiomer" refers to a compound that is present in greater than 90% enantiomeric excess, such as greater than 95%, greater than 96% ee, greater than 97% ee, greater than 98% ee, or greater than 99% ee.

EXAMPLES

The present application now being generally described, it will be more readily understood by reference to the following examples which are included merely for purposes of illustration of certain aspects and embodiments of the present disclosure, and are not intended to limit the claimed invention.

For the examples provided below, the enantiomeric excess is determined after the basic amine, (syn)-3-acetamido-4-allyl-N-(tert-butyl)pyrrolidine-3-carboxamide from the crystallized salt is derivatized as its tert-butyl carbamate or Boc group. This product is analyzed by chiral HPLC using a Chiralpak IB 5 m (4.6 mm×250 mm) column. The specific details for preparation of the Boc-derivative and HPLC analysis are provided below as Examples 16 and 17 respectively.

Example 1: (syn)-3-acetamido-4-allyl-N-(tert-butyl) pyrrolidine-3-carboxamide (IIa and IIb)

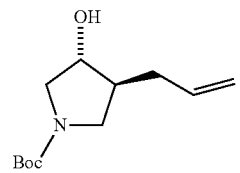 [SMILES: C=CC[C@H]1CN(C(=O)OC(C)(C)C)C[C@@H]1O]

Step 1: Synthesis of Racemic tert-butyl-trans-3-allyl-4-hydroxypyrrolidine-1-carboxylate Allyl magnesium bromide (1,037 mL, 713 mmol, 0.69 M in diethyl ether) was cooled to 0° C. and carefully treated with tert-butyl 6-oxa-3-azabicyclo[3.1.0]hexane-3-carboxylate (11, 60 g, 323.9 mmol) in anhydrous diethyl ether (324 mL, 1 M). After the addition was complete, the reaction mixture was stirred for 15 min, slowly quenched with saturated aqueous ammonium chloride (500 mL), extracted with diethyl ether (2×400 mL), dried over MgSO₄, filtered, and concentrated. Purification by flash column chromatography (20-4₀% ethyl acetate in heptane) gave tert-butyl-trans-3-allyl-4-hydroxypyrrolidine-1-carboxylate (12, 64.33 g, 87% yield) as a pale yellow oil. ¹H-NMR (CDCl₃, 400 MHz): δ 5.80 (1H, m), 5.06 (2H, m), 4.07 (1H, m), 3.57 (2H, m), 3.22 (1H, m), 3.08 (1H, m), 2.26-2.10 (2H, m) and 1.45 (9H, s).

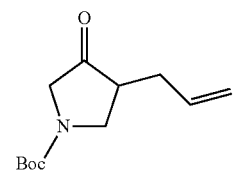

Step 2: Synthesis of Racemic tert-Butyl-3-allyl-4-oxopyrrolidine-1-carboxylate While under an atmosphere of dry nitrogen, an ice-cooled solution of tert-butyl-trans-3-allyl-4-hydroxypyrrolidine-1-carboxylate (12, 60 g, 264 mmol) and diisopropylethylamine (132.2 mL, 799.8 mmol) in dichloromethane (750 mL, 0.35 M) was treated dropwise with a solution of sulfur trioxide pyridine complex (94.95 g, 596.6 mmol) in anhydrous DMSO (750 mL) at a rate to keep the reaction mixture below 10° C. After the addition was complete, the mixture was stirred at 3° C. for 15 min, quenched with water (380 mL) and extracted with ethyl acetate (500 mL, then 2×300 mL). The combined organic solution was washed twice with water (200 mL), once with saturated aqueous sodium chloride (200 mL), dried (MgSO$_4$) and concentrated. The resulting crude oil was distilled at 105° C. (0.4 mm Hg) to afford racemic tert-butyl 3-allyl-4-oxopyrrolidine-1-carboxylate (13, 58 g, 83% yield) as a colorless oil. $^1$H-NMR (CDCl$_3$, 400 MHz): $\delta_H$: 5.74 (1H, m), 5.09 (2H, m), 4.02 (1H, m), 3.88 (1H, d, J=19.4 Hz), 3.68 (1H, d, J=19.4 Hz), 3.31 (1H, dd, J=9.4, 8.3 Hz), 2.65 (1H, m), 2.54 (1H, m), 2.18 (1H, m) and 1.45 (9H, s).

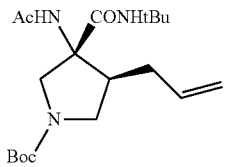

Step 3: Synthesis of Racemic (syn) tert-butyl-3-acetamido-4-allyl-3-(tert-butylcarbamoyl)pyrrolidine-1-carboxylate While under an atmosphere of dry nitrogen, a solution of ketone (13, 79.3 g, 352 mmol) and ammonium acetate (135.7 g, 1,759 mmol) in methanol (200 mL) was cooled to 0° C. and treated with tert-butyl isocyanide (80.2 mL, 704 mol) and stirred at room temperature for 48 h. The resulting slurry was concentrated, diluted with a 1:2 mixture of ethyl acetate and water (300 mL). After stirring for 1 h, the precipitate was filtered and washed with water (100 mL) and ice-cold ether (2×50 mL) and air dried. The crude product, which is predominately the syn-isomer (about 10:1), was diluted with ethyl acetate (400 mL), isopropyl alcohol (400 mL) and ethanol (2 mL), then warmed to 70° C. After stirring for an additional 2 h, the solution was allowed to cool to room temperature with continued stirring overnight, filtered and washed with ice-cooled ether (2×50 mL) and dried in the oven at 60° C. overnight to give racemic (syn) tert-butyl-3-acetamido-4-allyl-3-(tert-butylcarbamoyl)pyrrolidine-1-carboxylate (14, 82.1 g, 63% yield.) as a white powder.

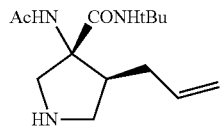

Step 4: Synthesis of Racemic (syn)-3-acetamido-4-allyl-N-(tert-butyl)pyrrolidine-3-carboxamide A solution of racemic (syn)-tert-butyl-3-acetamido-4-allyl-3-(tert-butylcarbamoyl)pyrrolidine-1-carboxylate (14, 20.0 g, 54.4 mmol) in dichloromethane (400 mL) was cooled to 0° C. and treated with trifluoroacetic acid (80 mL, 19.8 mmol) dropwise via addition funnel. The solution warmed to room temperature and stirred until, no starting material remained as indicated by TLC (about 1 h). The solution was concentrated, re-dissolved in toluene (50 mL) and concentrated (3×) to ensure removal of excess trifluoroacetic acid. The resulting white solid was dissolved in methanol (300 mL) and treated with DOWEX 550A-OH resin (approximately 120 g pre-washed with water and methanol). After stirring the resin solution (pH 8.5) for 2 h, the mixture was filtered and concentrated, re-dissolved in dichloromethane and concentrated to give racemic (syn)-3-acetamido-4-allyl-N-(tert-butyl)pyrrolidine-3-carboxamide (IIa and IIb, 14.4 g, 99%) as a white foam. $^1$H NMR (400 MHz, d$_4$ MeOH) $\delta$ 5.82-5.71 (m, 1H) 5.10-5.01 (m, 2H) 3.76 (d, J=11.9 Hz, 1H) 3.16 (dd, J=11.3, 7.6 Hz, 1H) 2.97 (d, J=11.9 Hz, 1H) 2.70 (dd, J=11.3, 7.1 Hz, 1H) 2.40-2.35 (m, 1H) 2.32-2.24 (m, 1H) 1.98 (s, 3H) 1.92-1.84 (m, 1H) 1.33 (s, 9H). FIG. 1 shows (IIa and IIb) by chiral HPLC.

Example 2: Preparation of (R)-2-((1-phenylethyl)carbamoyl)benzoic acid (3)

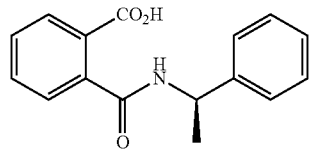 [SMILES: C[C@@H](NC(=O)c1ccccc1C(=O)O)c1ccccc1]

Synthesis of (R)-2-((1-phenylethyl)carbamoyl)benzoic acid (3)

A suspension of phthalic anhydride (50 g, 337.6 mmol) in EtOAc (200 mL) and THF (200 mL) was cooled to 5-10° C. with stirring and carefully treated with (R)-(+)-1-phenylethylamine (47.37 mL, 371.3 mmol). After the addition was complete the reaction became clear, the ice bath was removed and the solution stirred for 15 hours. The reaction mixture was diluted with ethyl acetate (200 mL), washed with 2N HCl, saturated aqueous sodium chloride and water, dried over sodium sulfate, filtered, and concentrated under reduced pressure. The crude product was recrystallized from MTBE and hexanes to give (R)-2-((1-phenylethyl)carbamoyl)benzoic acid (3, 64.6 g, 71%) as a white powder. NMR (400 MHz, DMSO) $\delta$ 8.67 (d, J=8.2 Hz, 1H) 7.72 (dd, J=7.6, 1.3 Hz, 1H) 7.53 (td, J=7.6, 1.4 Hz, 1H) 7.45 (td, J=7.6, 1.4 Hz, 1H) 7.38-7.35 (m, 3H) 7.27 (t, J=7.6 Hz, 2H) 7.20-7.09 (m, 1H) 5.09-5.02 (m, 1H) 1.37 (d, J=7.0 Hz, 3H).

Example 3: Preparation of (2S,3S)-2,3-bis(benzoyloxy)-4-(dimethylamino)-4-oxobutanoic acid

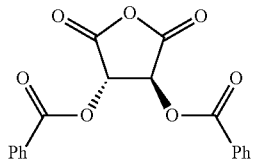 [SMILES: O=C(O[C@@H]1C(=O)OC(=O)[C@H]1OC(=O)c1ccccc1)c1ccccc1]

Step 1: Synthesis of (3S,4S)-2,5-dioxotetrahydrofuran-3,4-diyl dibenzoate

A suspension of (+)-2,3-dibenzoyl-D-tartaric acid (300 g, 358.3 mmol) in acetic anhydride (600 mL) was warmed to 85° C. with stirring. After 2 h, the solution was cooled in an ice bath and the resulting suspension was filtered, washed with 1:1 hexanes/diethyl ether (500 mL) and dried in vacuo to afford (3S,4S)-2,5-dioxotetrahydrofuran-3,4-diyl dibenzoate (239 g, 84% yield) as a white crystalline solid. NMR (400 MHz, CDCl$_3$) δ 8.08-8.06 (m, 4H) 7.67-7.63 (m, 2H) 7.51-7.47 (m, 4H) 5.98 (s, 2H).

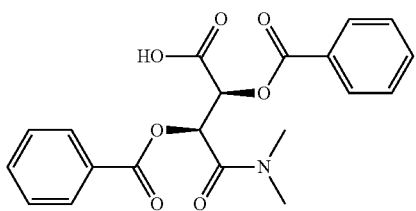

Step 2: Synthesis of (2S,3S)-2,3-bis(benzoyloxy)-4-(dimethylamino)-4-oxobutanoic acid A solution of (3S,4S)-2,5-dioxotetrahydrofuran-3,4-diyl dibenzoate (90 g, 264.5 mmol) in ethyl acetate (150 mL) was cooled to 0° C. and carefully treated with 2M dimethylamine in THF (158.7 mL, 317.4 mmol). Once the addition was complete, the ice bath was removed and the solution stirred for an additional 2 h, then sequentially washed with 2 N HCl, saturated aqueous sodium chloride, dried over sodium sulfate, filtered and concentrated. The crude product was recrystallized from MTBE and hexanes to give (2S,3S)-2,3-bis(benzoyloxy)-4-(dimethylamino)-4-oxobutanoic acid (4, 81 g, 79% yield) as a white powder. NMR (400 MHz, CDCl$_3$) δ 8.04-8.00 (m, 4H) 7.56-7.52 (m, 2H) 7.42-7.37 (m, 4H) 6.22 (d, J=6.0 Hz, 1H) 5.95 (d, J=6.0 Hz, 1H) 3.18 (s, 3H) 2.97 (s, 3H).

Example 4: Preparation of (2S,3S)-2,3-bis(benzoyloxy)-4-(diethylamino)-4-oxobutanoic acid

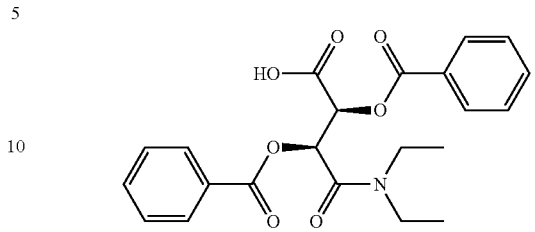

While under nitrogen, a suspension of (3S,4S)-2,5-dioxotetrahydrofuran-3,4-diyl dibenzoate (1.021 g, 3.0 mmol) in anhydrous THF (15 mL) was cooled in an ice bath, and treated with diethylamine (0.6 mL, 5.8 mmol). Once the addition was complete, the mixture was allowed to warm to room temperature over 1 h, with continued stirring for 16 h. The solution was treated with DOWEX 50W-X8 acid resin (3 g, prewashed with methanol), stirred a few minutes, filtered and the filtrate concentrated. The residual oil was dissolved in ethyl acetate (10 mL) and hexane (20 mL) while stirring. After stirring for 15 min, the resulting suspension was cooled in an ice-bath for 15 min, filtered and rinsed with 3:1 hexane/ethyl acetate. The solid was dried to afford (2S,3S)-2,3-bis(benzoyloxy)-4-(diethylamino)-4-oxobutanoic acid (5, 896 mg, 72% yield) as a white powder. NMR (400 MHz, CDCl$_3$) δ 8.04-7.99 (m, 4H) 7.55-7.50 (m, 2H) 7.40-7.36 (m, 4H) 6.19 (d, J=5.9 Hz, 1H) 5.95 (d, J=5.9 Hz, 1H) 3.55-3.44 (m, 3H) 3.27-3.18 (m, 1H) 1.23 (t, J=7.1 Hz, 3H) 1.05 (t, J=7.1 Hz, 3H).

Example 5: Preparation of (2S,3S)-2,3-bis(benzoyloxy)-4-oxo-4-(pyrrolidin-1-yl)butanoic acid

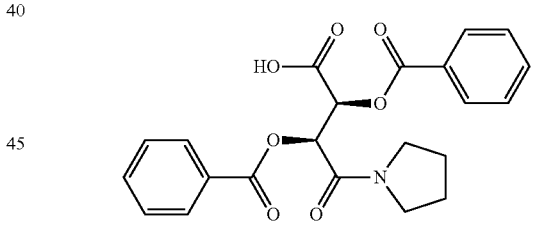

While under nitrogen, a suspension of (3S,4S)-2,5-dioxotetrahydrofuran-3,4-diyl dibenzoate (2.04 g, 6.0 mmol) in anhydrous THF (30 mL) was cooled in an ice bath, and treated with pyrrolidine (0.96 mL, 11.7 mmol). Once the addition was complete, the mixture was allowed to warm to room temperature over 1 h, with continued stirring for 16 h. The solution was treated with DOWEX 50W-X8 acid resin (6 g, prewashed with methanol), stirred a few minutes, filtered and the filtrate concentrated. The residual oil was dissolved in dichloromethane and loaded onto a silica gel column (~100 cc) and eluted sequentially with ethyl acetate, 10% methanol in ethyl acetate, and 88:12:2 ethyl acetate/methanol/acetic acid to afford (2S,3S)-2,3-bis(benzoyloxy)-4-oxo-4-(pyrrolidin-1-yl)butanoic acid (6, 1.94 g, 79% yield) as a white foam. NMR (400 MHz, CDCl3) δ 8.05-8.00 (m, 4H) 7.57-7.53 (m, 2H) 7.42-7.38 (m, 4H) 6.06 (dd, J=6.4 Hz, 1H) 5.94 (dd, J=6.3 Hz, 1H) 3.82-3.76 (m, 1H) 3.57-3.51 (m, 2H) 3.46-3.40 (m, 1H) 1.97-1.72 (m, 4H).

Example 6: Preparation of (2S,3S)-2,3-bis(benzoyloxy)-4-(isopropylamino)-4-oxobutanoic acid

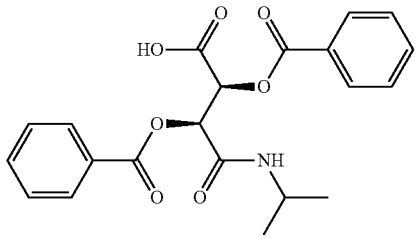 [SMILES: CC(C)NC(=O)[C@@H](OC(=O)c1ccccc1)[C@H](OC(=O)c1ccccc1)C(=O)O]

A solution of (3S,4S)-2,5-dioxotetrahydrofuran-3,4-diyl dibenzoate (88 g, 258.6 mmol) in ethyl acetate (132 mL) and THF (132 mL) was cooled to 0° C. and carefully treated with 2-aminopropane (26.6 mL, 310.3 mmol). Once the addition was complete, the ice bath was removed and the solution stirred for an additional 2 h, then sequentially washed with 2 N HCl, saturated aqueous sodium chloride, dried over sodium sulfate, filtered and concentrated. The crude product was recrystallized from MTBE and hexanes to give (2S,3S)-2,3-bis(benzoyloxy)-4-(isopropylamino)-4-oxobutanoic acid (7, 97.4 g, 94% yield) as a white powder. NMR (400 MHz, CDCl$_3$) δ 8.05-8.01 (m, 4H) 7.67-7.51 (m, 2H) 7.48-7.40 (m, 4H) 6.02 (d, J=3.4 Hz, 1H) 5.98 (d, J=3.4 Hz, 1H) 4.12-4.04 (m, 1H) 1.09 (d, J=6.6 Hz, 3H) 1.06 (d, J=6.6 Hz, 3H).

Example 7: Preparation of (3S,4S)-5-(isopropylamino)-3,4-bis((4-methylbenzoyl)oxy)-2,5-dioxopentanoic acid (8)

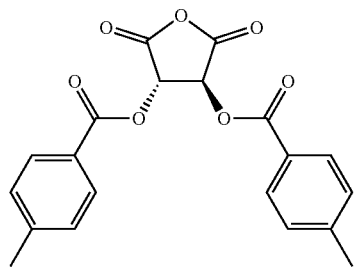 [SMILES: Cc1ccc(C(=O)O[C@@H]2C(=O)OC(=O)[C@H]2OC(=O)c2ccc(C)cc2)cc1]

Step 1: Synthesis of (3S,4S)-2,5-dioxotetrahydrofuran-3,4-diyl bis(4-methylbenzoate)

A suspension of (+)-2,3-di-O-toluoyl-D-tartaric acid (15.0 g, 38.82 mmol) in acetic anhydride (45 mL) was warmed to 85° C. with stirring. After 2 h, the solution was cooled in an ice bath and the resulting suspension was filtered, washed with 1:1 hexanes/diethyl ether (100 mL) and dried in vacuo to afford (3S,4S)-2,5-dioxotetrahydrofuran-3,4-diyl bis(4-methylbenzoate) (10.85 g, 76%) as a white crystalline solid. NMR (400 MHz, CDCl$_3$) δ 7.95 (d, J=8.3 Hz, 4H) 7.28 (d, J=8.3 Hz, 4H) 5.92 (s, 2H) 2.42 (s, 6H).

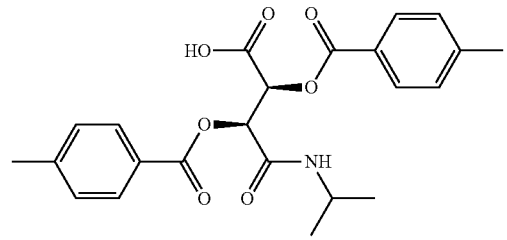

Step 2: Synthesis of (3S, 4S)-5-(isopropylamino)-3,4-bis((4-methylbenzoyl)oxy)-2,5-dioxopentanoic acid A suspension of (3S,4S)-2,5-dioxotetrahydrofuran-3,4-diyl bis(4-methylbenzoate) (5.0 g, 13.57 mmol) in ethyl acetate (20 mL) and THF (20 mL) was cooled to 0° C. and treated with 2-aminopropane (1.40 mL, 16.29 mmol). Upon addition the suspension became thick. The ice bath was removed and stirring continued for an additional 1 h. Dichloromethane (100 mL) was added and the solution was sequentially washed with 2 N HCl, saturated aqueous sodium chloride, dried over sodium sulfate, filtered, and concentrated. The crude product was recrystallized from MTBE and hexanes to give (3S,4S)-5-(isopropylamino)-3,4-bis((4-methylbenzoyl)oxy)-2,5-dioxopentanoic acid (8, 5.62 g, 97%) as a white powder. NMR (400 MHz, CDCl$_3$) δ 7.94-7.90 (m, 4H) 7.25 (d, J=7.8 Hz, 2H) 7.21 (d, J=8.0 Hz, 2H) 5.99 (d, J=3.5 Hz, 1H) 5.95 (d, J=3.5 Hz, 1H) 4.12-4.03 (m, 1H) 2.41 (s, 3H) 2.39 (s, 3H) 1.08 (d, J=6.6 Hz, 3H) 1.06 (d, J=6.5 Hz, 3H).

Example 8: Selective Crystallization of Racemic (syn)-3-acetamido-4-allyl-N-(tert-butyl)pyrrolidine-3-carboxamide (IIa and IIb) with (R)-2-((1-phenylethyl)carbamoyl)benzoic acid (3)

Figure 2:
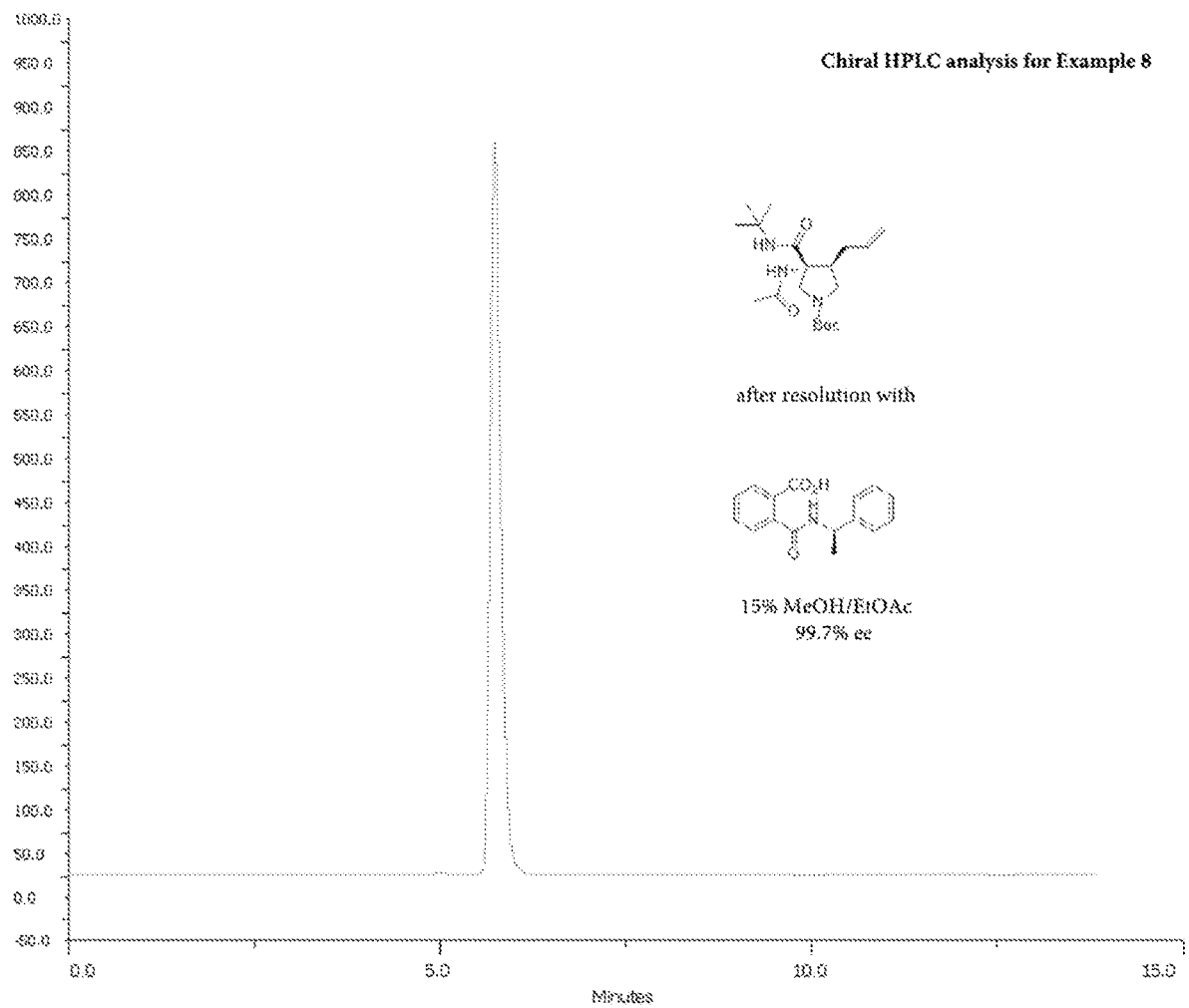
FIG. 2 shows the results of the chiral HPLC analysis for the crystalline product of Example 8.

A solution of racemic (syn)-3-acetamido-4-allyl-N-(tert-butyl)pyrrolidine-3-carboxamide (150 mg, 0.5 mmol), (R)-2-((1-phenylethyl)carbamoyl)benzoic acid (83 mg, 0.55 eq) and acetic acid (17 mg, 0.5 eq) in 25% methanol/ethyl acetate (18 mL) was warmed until the solution became clear. After the solution was allowed to cool to ambient temperature, the salt slowly crystallized from the solution. After about 48 h, the resulting crystalline material was filtered, washed with an ice-cooled solution of 25% methanol/ethyl acetate and dried to give the enriched salt (34% yield, 99.7% ee). FIG. 2 shows the salt of Example 8 by chiral HPLC.

Example 9: Selective Crystallization of Racemic (syn)-3-acetamido-4-allyl-N-(tert-butyl)pyrrolidine-3-carboxamide (IIa and IIb) with (R)-2-((1-phenylethyl)carbamoyl)benzoic acid (3)

Figure 3:
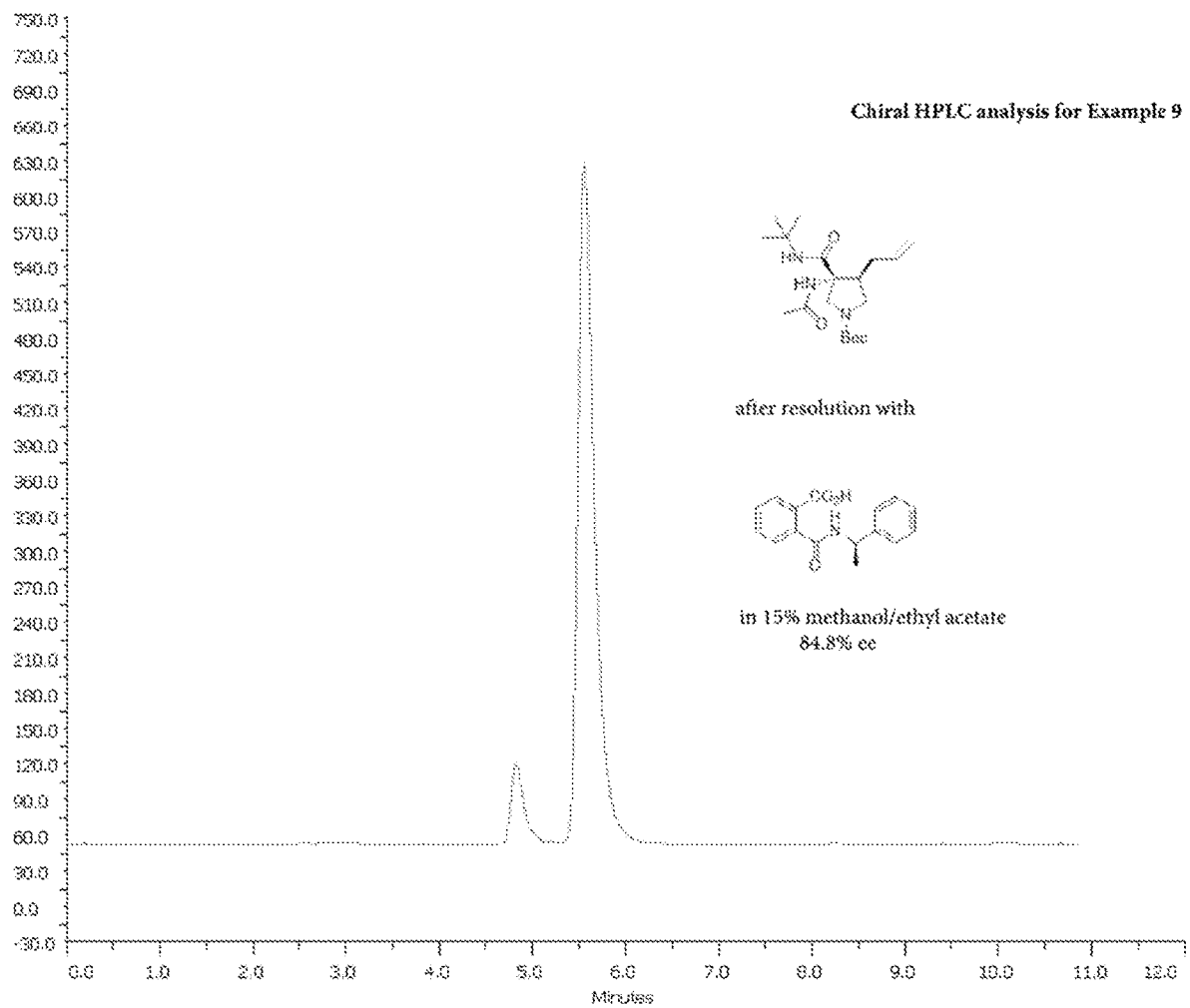
FIG. 3 shows the results of the chiral HPLC analysis for the crystalline product of Example 9.

A solution of racemic (syn)-3-acetamido-4-allyl-N-(tert-butyl)pyrrolidine-3-carboxamide (75 mg, 0.28 mmol) and (R)-2-((1-phenylethyl)carbamoyl)benzoic acid (76 mg, 0.28 eq) in 15% methanol/ethyl acetate (4 mL) was warmed until the solution became clear. After the solution was allowed to cool to ambient temperature, the salt slowly crystallized from the solution. After about 24 h the resulting crystalline material was filtered, washed with an ice-cooled solution of 15% methanol/ethyl acetate and dried to give the enriched salt (66% yield, 84.8% ee). FIG. 3 shows the salt of Example 9 by chiral HPLC.

Example 10: Selective Crystallization of Racemic (syn)-3-acetamido-4-allyl-N-(tert-butyl)pyrrolidine-3-carboxamide (IIa and IIb) with (2S,3S)-2,3-bis(benzoyloxy)-4-(dimethylamino)-4-oxobutanoic acid (4)

Figure 4:
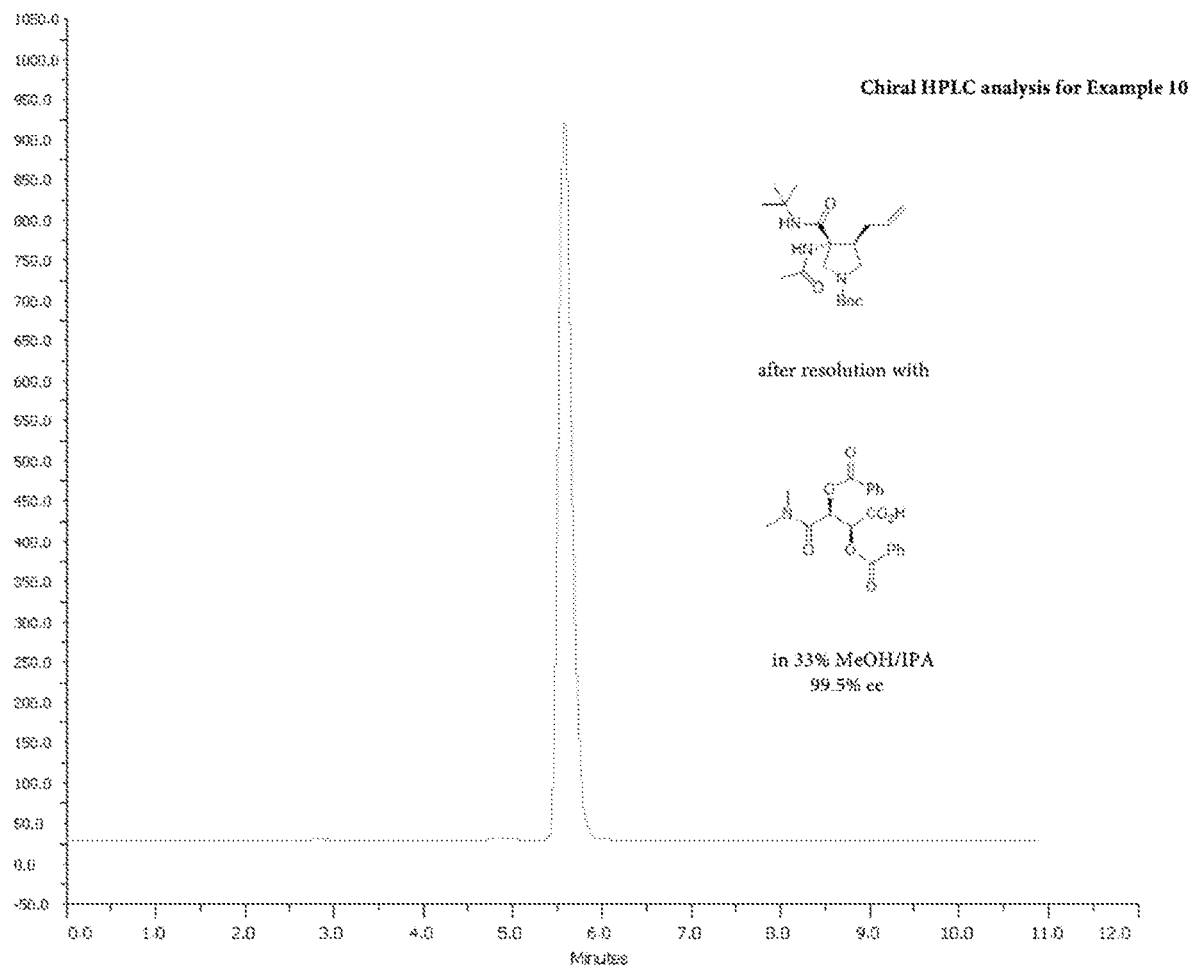
FIG. 4 shows the results of the chiral HPLC analysis for the crystalline product of Example 10.

A solution of racemic (syn)-3-acetamido-4-allyl-N-(tert-butyl)pyrrolidine-3-carboxamide (1.65 g, 6.17 mmol) in methanol (9 mL) was treated with a second solution of (2S,3S)-2,3-bis(benzoyloxy)-4-(dimethylamino)-4-oxobutanoic acid (2.37 g, 6.17 mmol) in warm isopropanol (41 mL). After the solutions were combined and allowed to cool to ambient temperature, the salt slowly crystallized from the solution (48-72 h). This resulting crystalline material was filtered, washed with an ice-cooled solution of 33% methanol/isopropanol and dried to give the enriched salt (77% yield, 99.5% ee). FIG. 4 shows the salt of Example 10 by chiral HPLC.

Example 11: Selective Crystallization of Racemic (syn)-3-acetamido-4-allyl-N-(tert-butyl)pyrrolidine-3-carboxamide (IIa and IIb) with (2S,3S)-2,3-bis(benzoyloxy)-4-(diethylamino)-4-oxobutanoic acid (5)

Figure 5:
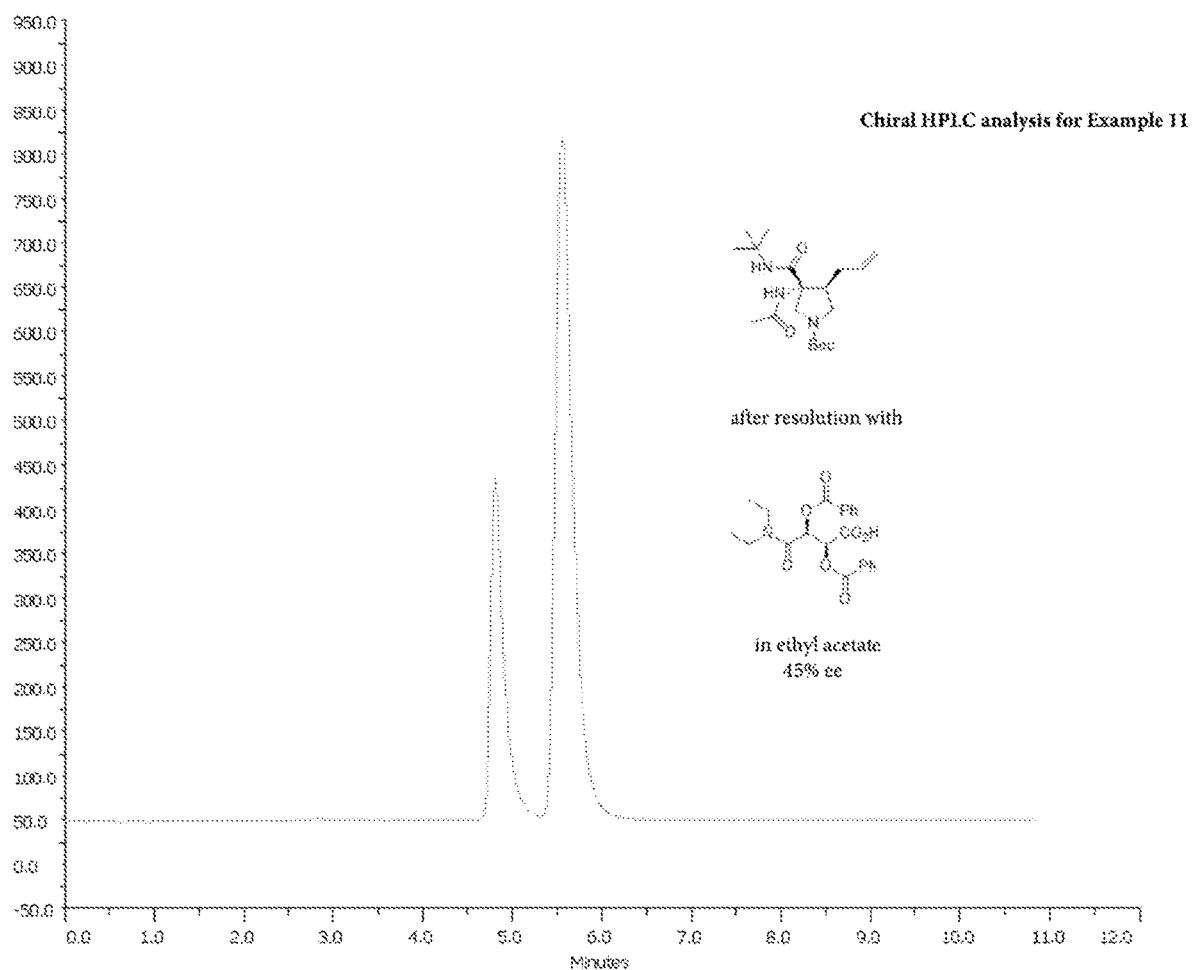
FIG. 5 shows the results of the chiral HPLC analysis for the crystalline product of Example 11.

A solution of racemic (syn)-3-acetamido-4-allyl-N-(tert-butyl)pyrrolidine-3-carboxamide (75 mg, 0.28 mmol) and (2S,3S)-2,3-bis(benzoyloxy)-4-(diethylamino)-4-oxobutanoic acid (116 mg, 0.28 mmol) in ethyl acetate (3 mL) was warmed until the solution became clear. After the solution was allowed to cool to ambient temperature, the salt slowly crystallized from the solution. After about 24 h the resulting crystalline material was filtered, washed with ice cold ethyl acetate and dried to give the enriched salt (84% yield, 45% ee). FIG. 5 shows the salt of Example 11 by chiral HPLC.

Example 12: Selective Crystallization of Racemic (syn)-3-acetamido-4-allyl-N-(tert-butyl)pyrrolidine-3-carboxamide (IIa and IIb) with (2S,3S)-2,3-bis(benzoyloxy)-4-oxo-4-(pyrrolidin-1-yl)butanoic acid (6)

Figure 6:
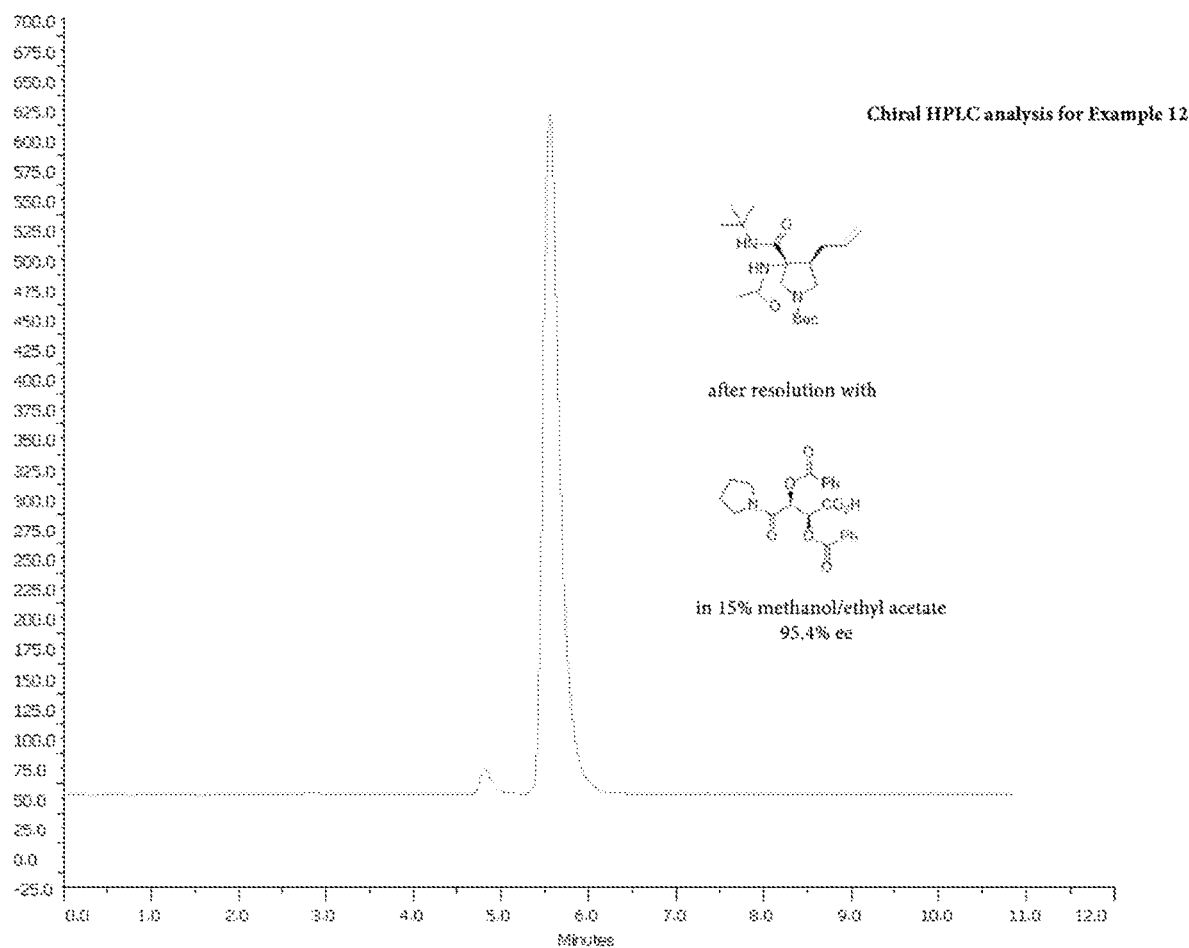
FIG. 6 shows the results of the chiral HPLC analysis for the crystalline product of Example 12.

A solution of racemic (syn)-3-acetamido-4-allyl-N-(tert-butyl)pyrrolidine-3-carboxamide (75 mg, 0.28 mmol) and (2S,3S)-2,3-bis(benzoyloxy)-4-oxo-4-(pyrrolidin-1-yl)butanoic acid (115 mg, 0.28 mmol) in 15% methanol/ethyl acetate (4 mL) was warmed until the solution became clear. After the solution was allowed to cool to ambient temperature, the salt slowly crystallized from the solution. After about 24 h the resulting crystalline material was filtered, washed with an ice-cooled solution of 15% methanol/ethyl acetate and dried to give the enriched salt (73% yield, 95.4% ee). FIG. 6 shows the salt of Example 12 by chiral HPLC.

Example 13: Selective Crystallization of Racemic (syn)-3-acetamido-4-allyl-N-(tert-butyl)pyrrolidine-3-carboxamide (IIa and IIb) with (2S,3S)-2,3-bis(benzoyloxy)-4-(isopropylamino)-4-oxobutanoic acid (7)

Figure 7:
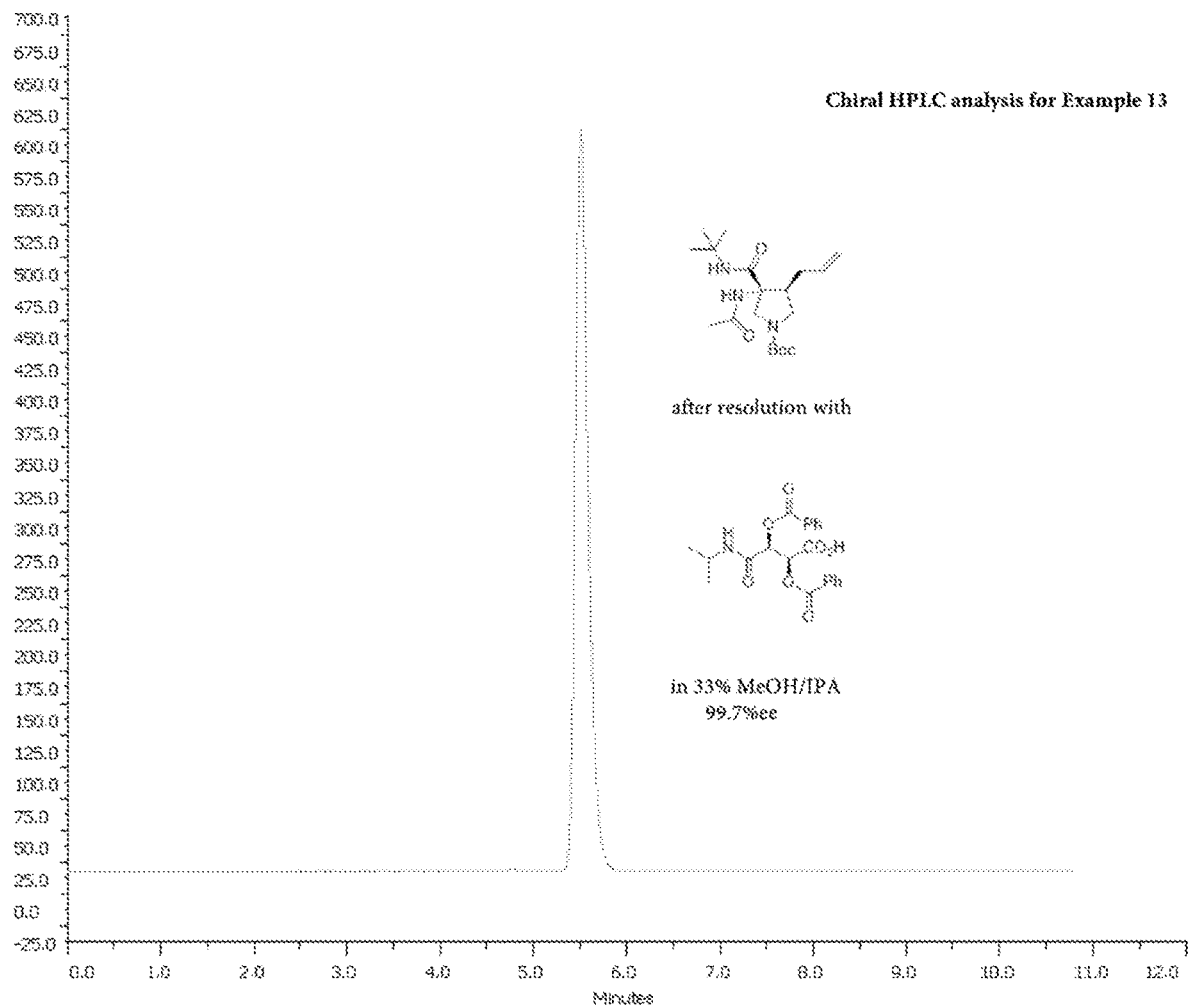
FIG. 7 shows the results of the chiral HPLC analysis for the crystalline product of Example 13.

A solution of racemic (syn)-3-acetamido-4-allyl-N-(tert-butyl)pyrrolidine-3-carboxamide (1.65 g, 6.17 mmol) in isopropanol (20 mL) was treated with a second solution of (2S,3S)-2,3-bis(benzoyloxy)-4-(isopropylamino)-4-oxobutanoic acid (2.46 g, 6.17 mmol) in warm 55% methanol/isopropanol (30 mL). After the solutions are combined and allowed to cool to ambient temperature, the desired salt slowly crystallizes from the solution. After about 48 h the resulting crystalline material is filtered, washed with an ice-cooled solution of 33% methanol/isopropanol and dried to give the enriched salt (77% yield, 99.7% ee). FIG. 7 shows the salt of Example 13 by chiral HPLC.

Example 14: Selective Crystallization of Racemic (syn)-3-acetamido-4-allyl-N-(tert-butyl)pyrrolidine-3-carboxamide (IIa and IIb) with (2S,3S)-2,3-bis(benzoyloxy)-4-(isopropylamino)-4-oxobutanoic acid (7)

Figure 8:
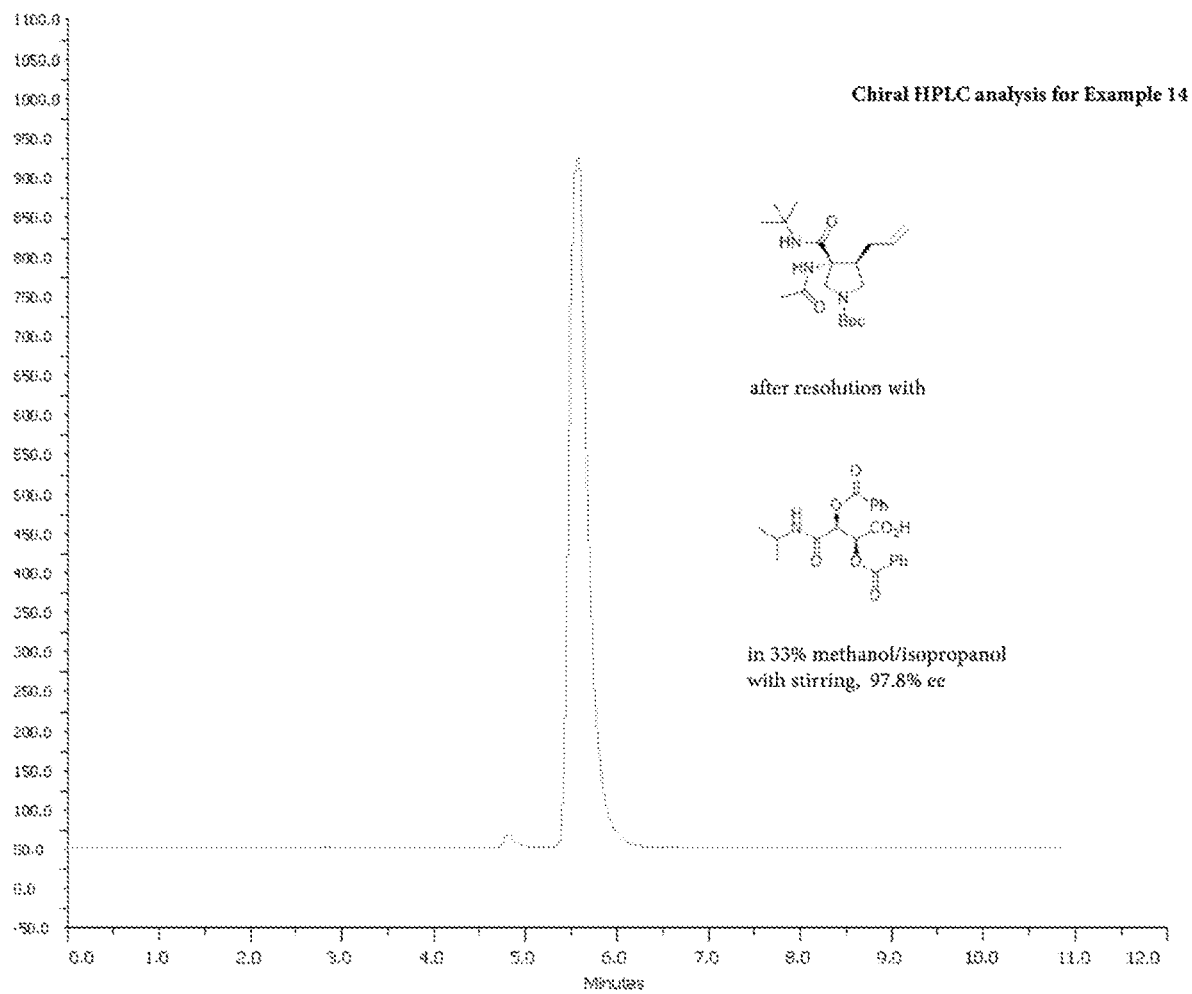
FIG. 8 shows the results of the chiral HPLC analysis for the crystalline product of Example 14.

A stirred solution of racemic (syn)-3-acetamido-4-allyl-N-(tert-butyl)pyrrolidine-3-carboxamide (0.83 g 3.10 mmol) in isopropanol (10 mL) was treated with a second solution of (2S,3S)-2,3-bis(benzoyloxy)-4-(isopropylamino)-4-oxobutanoic acid (1.24 g, 3.10 mmol) in warm 55% methanol/isopropanol (15 mL). With continued stirring, the solutions are combined and allowed to cool to ambient temperature. After about 24 h the resulting crystalline material is filtered, washed with an ice-cooled solution of 33% methanol/isopropanol and dried to give the enriched salt (81% yield, 97.8% ee). FIG. 8 shows the salt of Example 14 by chiral HPLC.

Example 15: Selective Crystallization of Racemic (syn)-3-acetamido-4-allyl-N-(tert-butyl)pyrrolidine-3-carboxamide (IIa and IIb) with (3S,4S)-5-(isopropylamino)-3,4-bis((4-methylbenzoyl)oxy)-2,5-dioxopentanoic acid (8)

Figure 9:
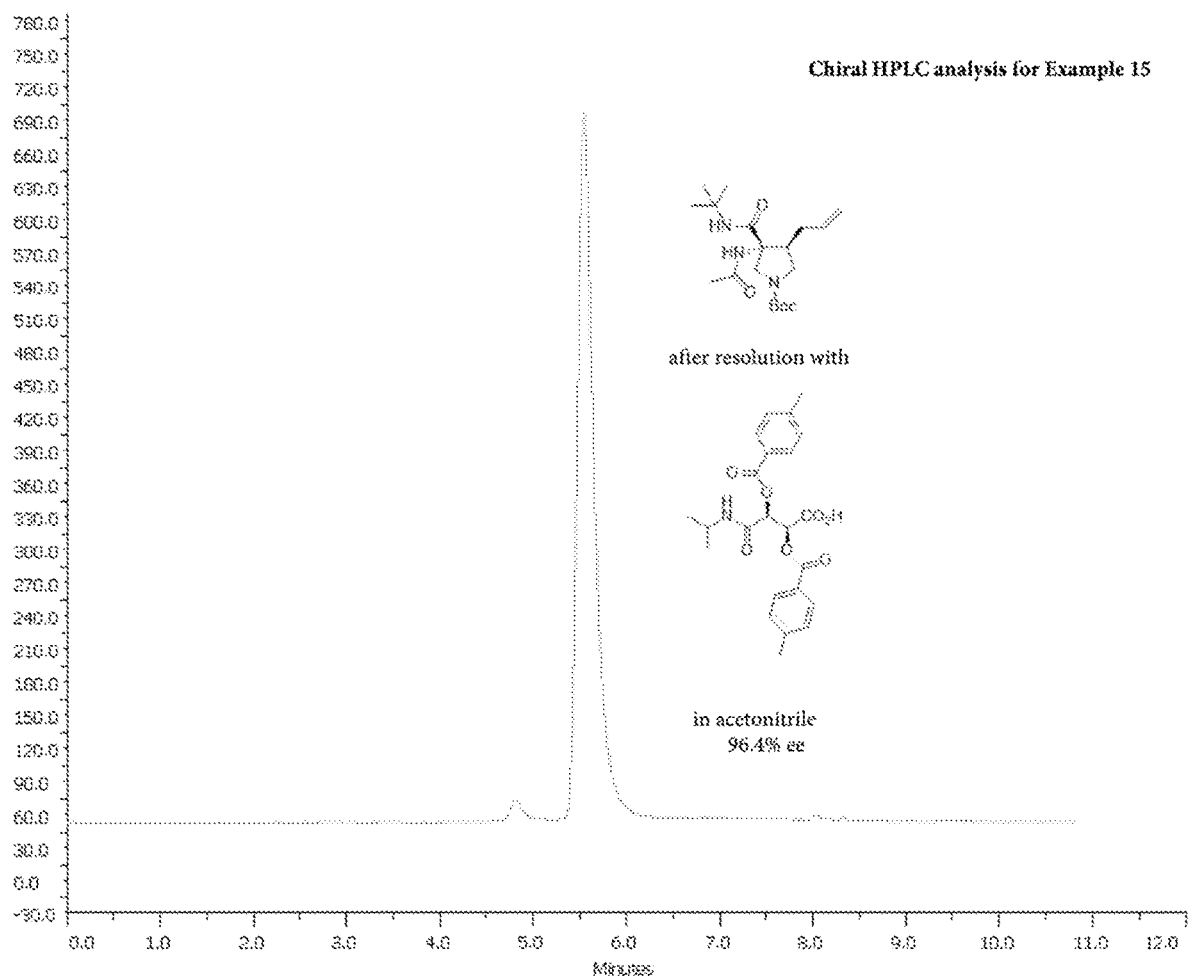
FIG. 9 shows the results of the chiral HPLC analysis for the crystalline product of Example 15.

A solution of racemic (syn)-3-acetamido-4-allyl-N-(tert-butyl)pyrrolidine-3-carboxamide (75 mg, 0.28 mmol) and (3S,4S)-5-(isopropylamino)-3,4-bis((4-methylbenzoyl)oxy)-2,5-dioxopentanoic acid (120 mg, 0.28 mmol) in acetonitrile (1 mL) was warmed until the solution became clear. After the solution was allowed to cool to ambient temperature, the desired salt slowly crystallizes from the solution. After about 24 h the resulting crystalline material was filtered, washed with ice cold acetonitrile and dried to give the enriched salt (46% yield, 96.4% ee). FIG. 9 shows the salt of Example 15 by chiral HPLC.

Example 16: General Method for the Preparation of Chiral (syn) tert-butyl-3-acetamido-4-allyl-3-(tert-butylcarbamoyl)pyrrolidine-1-carboxylate from the Selective Crystallizations (examples 8-15)

A solution of the selectively crystallized salt (100 mg) in ethyl acetate (1 mL) and saturated aqueous $NaHCO_3$ (1 mL) is treated with di-tert-butyl dicarbonate (1.5 equiv.). After stirring for 16-24 h, the organic layer is separated, filtered through a short pad of silica gel eluting with 30% ethyl acetate/hexane then 100% ethyl acetate and concentrated to give (syn) tert-butyl-3-acetamido-4-allyl-3-(tert-butylcarbamoyl)pyrrolidine-1-carboxylate as a white solid that is analyzed by chiral HPLC.

Example 17: Chiral HPLC Method to Determine Enantiomeric Excess of (syn) tert-butyl-3-acetamido-4-allyl-3-(tert-butylcarbamoyl)pyrrolidine-1-carboxylate (IIa)

Samples are analyzed by HPLC using a Gilson 215 Liquid Handler equipped with a PrepELS II Detector, Daicel Corporation Chiralpak IB 5 m (4.6 mm×250 mm) column using 10% ethanol/hexane, isocratic over 12 minutes with a flow rate of 1 mL/min.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the present disclosure have been discussed, the above specification is illustrative and not restrictive. Many variations of the embodiments will become apparent to those skilled in the art upon review of this specification and the claims below. The full scope of the claimed invention should be determined by reference to the claims, along with their full scope of equivalents, and the specification, along with such variations.

The invention claimed is:

1. A salt of an amine compound represented by formula I and a carboxylic acid compound represented by formula A or B:

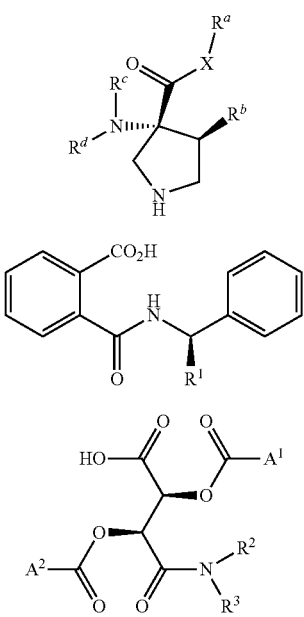

wherein:
X is O, S, or NR$^e$;
R$^a$ is H, lower alkyl, or lower cycloalkyl;
R$^b$ is —CH$_2$CH=CH$_2$, —(CH$_2$)$_n$CH$_2$Z$^1$, —(CH$_2$)$_n$C(O)H, or —(CH$_2$)$_n$CO$_2$Z$^2$;
R$^c$ and R$^d$ are independently H, lower alkyl, lower cycloalkyl, silyl, acyl, acyloxy; or R$^c$ and R$^d$, together with the N that links them, form an optionally substituted 3- to 6-membered heteroaryl or heterocyclic ring;
R$^e$ is H or lower alkyl;
n is 1 or 2;

Z$^1$ is halogen, alkyl sulfonate, aryl sulfonate, or an alkyl sulfonate optionally substituted with one or more halogen;
Z$^2$ is H, lower alkyl, or lower cycloalkyl;
A$^1$ is phenyl or 5-6 membered heteroaryl, and is optionally substituted by up to 4 R$^4$;
A$^2$ is phenyl or 5-6 membered heteroaryl, and is optionally substituted by up to 4 R$^5$;
R$^1$ is lower alkyl or lower cycloalkyl;
R$^2$ and R$^3$ are independently H, lower alkyl, or lower cycloalkyl; or R$^2$ and R$^3$, together with the N that links them, form an optionally substituted 3- to 6-membered saturated heterocyclic ring optionally containing 1 or 2 additional heteroatoms selected from S or O; and
R$^4$ and R$^5$ are independently halogen, hydroxyl, nitro, lower alkyl, or lower cycloalkyl.

2. The salt of claim 1, wherein A$^1$ and A$^2$ are phenyl.

3. The salt of claim 1, wherein A$^1$ is substituted by one R$^4$ and A$^2$ is substituted by one R$^5$.

4. The salt of claim 1, wherein the carboxylic acid compound is represented by formula A or B-I:

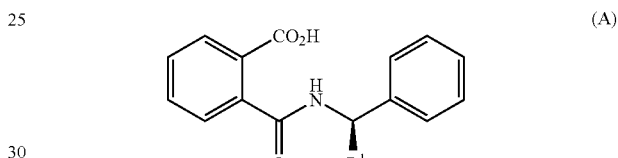

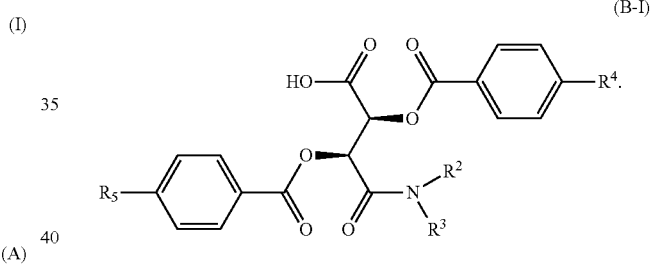

5. The salt of claim 1, wherein the amine compound in the salt has an enantiomeric excess of at least 75% ee.

6. The salt of claim 5, wherein the carboxylic acid compound in the salt is essentially a single enantiomer.

7. The salt of claim 1, wherein R$^a$ is tent-butyl.

8. The salt of claim 1, wherein R$^b$ is —CH$_2$CH=CH$_2$.

9. The salt of claim 1, wherein R$^c$ is H.

10. The salt of claim 1, wherein R$^d$ is acetyl or trifluoroacetyl.

11. The salt of claim 1, wherein X is NH.

12. The salt of claim 1, wherein X is O.

13. The salt of claim 1, wherein the amine compound is:

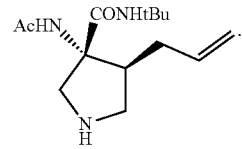

14. The salt of claim 1, wherein the carboxylic acid compound is represented by formula A.

15. The salt of claim 14, wherein R$^1$ is methyl.

16. The salt of claim 1, wherein the carboxylic acid compound is represented by formula B.

17. The salt of claim 4, wherein the carboxylic acid compound is represented by formula B-I.

18. The salt of claim 16, wherein $R^2$ and $R^3$ are independently methyl, ethyl, or isopropyl; or $R^2$ and $R^3$, together with the N that links them, form a pyrrolidinyl.

19. The salt of claim 17, wherein $R^4$ is methyl.

20. The salt of claim 17, wherein $R^5$ is methyl.

21. The salt of claim 1, wherein the carboxylic acid compound is:

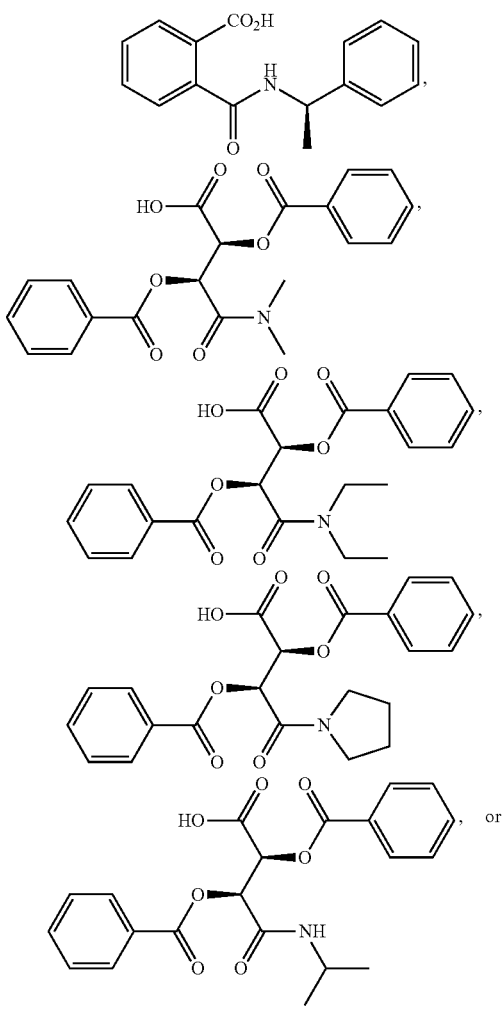

-continued

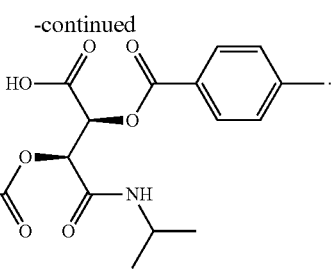

22. A method of preparing the salt of claim 1 by fractional crystallization, comprising:

preparing a crystallization solution comprising the amine compound, essentially a single enantiomer of the carboxylic acid compound, and a solvent; and crystallizing from the crystallization solution the salt of the amine compound and the carboxylic acid compound.

23. The method of claim 22, wherein the solvent comprises water, methanol, ethanol, isopropanol, ethyl acetate, or acetonitrile or a mixture of any of these.

24. The method of claim 22, wherein the amine compound in the salt crystallized from the crystallization solution is enantiomerically enriched relative to the amine compound present in the crystallization solution prior to crystallization.

25. The method of claim 22, wherein the amine compound in the crystallization solution is racemic.

26. The method of claim 22, wherein the amine compound in the crystallization solution is enantiomerically enriched.

27. The method of claim 22, wherein preparing the crystallization solution comprises:

preparing a precursor solution comprising the amine compound, a second enantiomer of the amine compound, and a second enantiomer of the carboxylic acid compound;

crystallizing from the precursor solution the salt of the second enantiomer of the amine compound with the second enantiomer of the carboxylic acid compound, thereby forming the crystallization solution as the supernatant.

* * * * *